US005922615A

United States Patent [19]

[11] Patent Number: 5,922,615

[45] Date of Patent: Jul. 13, 1999

Nowakowski et al.

[54] ASSAY DEVICES COMPRISING A POROUS CAPTURE MEMBRANE IN FLUID-WITHDRAWING CONTACT WITH A NONABSORBENT CAPILLARY NETWORK

[75] Inventors: Mark R. Nowakowski; Kenneth F. Buechler, both of San Diego; Richard R. Anderson, Encinitas; Gunars E. Valkirs, Escondido, all of Calif.

[73] Assignee: Biosite Diagnostics Incorporated, San Diego, Calif.

[21] Appl. No.: 08/458,276

[22] Filed: Jun. 2, 1995

Related U.S. Application Data

[63] Continuation of application No. 08/380,145, Jan. 27, 1995., abandoned, which is a continuation of application No. 07/961,267, Oct. 14, 1992., abandoned, which is a continuation-in-part of application No. 07/500,299, Mar. 12, 1990., abandoned

[51] Int. Cl.$^{6}$ .................................................. G01N 33/543

[52] U.S. Cl. .......................... 436/518; 435/7.1; 435/7.92; 435/7.93; 435/7.94; 435/7.95; 435/970; 435/975; 436/501; 436/535; 436/805; 436/810

[58] Field of Search .......................... 435/7.1, 7.92–7.95, 435/805, 808, 970, 975; 436/518, 528, 535, 539, 540, 501, 541, 544, 805, 807.81

[56] References Cited

U.S. PATENT DOCUMENTS

| | | | |
|---|---|---|---|
| 3,810,739 | 5/1974 | Nussbaum | 435/805 X |
| 4,233,029 | 11/1980 | Columbus | 422/58 X |
| 4,366,241 | 12/1982 | Tom et al. | 435/7.1 |
| 4,459,361 | 7/1984 | Gefter | 436/523 |
| 5,073,484 | 12/1991 | Swanson et al. | 435/7.92 |
| 5,458,852 | 10/1995 | Buechler | 422/58 |
| 5,654,162 | 8/1997 | Guire et al. | 435/7.92 |
| 5,736,188 | 4/1998 | Alcocki et al. | 427/2.11 |
| B1 4,366,241 | 10/1988 | Tom et al. | 435/7.9 |

FOREIGN PATENT DOCUMENTS

| | | | |
|---|---|---|---|
| 0239174 | 3/1987 | European Pat. Off. | 422/58 |

*Primary Examiner*—Carol A. Spiegel
*Attorney, Agent, or Firm*—Lyon & Lyon LLP

[57] ABSTRACT

Devices for use in heterogeneous ligand-receptor assays, having a porous member in contact with a nonabsorbent textured surface, where the surface texturing is such that a capillary network is formed when in fluid communication with the porous member. More particularly, these devices comprise:

(a) a porous member having (i) at least one binding agent capable of immobilizing at least one target ligand on the porous member from a fluid sample in at least one zone and (ii) a means for detecting the presence or amount of said target ligand as a result of the assay process; and (b) a nonabsorbent member in fluid communication with the porous member, the nonabsorbent member forming at least one capillary with the porous member so that when sample, alone or in combination with other fluids, is added to the porous member, fluid is drawn through the porous member.

45 Claims, 7 Drawing Sheets

ASSAY DEVICES COMPRISING A POROUS CAPTURE MEMBRANE IN FLUID-WITHDRAWING CONTACT WITH A NONABSORBENT CAPILLARY NETWORK

This application is a continuation of prior application U.S. Ser. No. 08/380,145 filed Jan. 27, 1995, now abandoned, which is a continuation of prior application U.S. Ser. No. 07/961,267, filed Oct. 14, 1992, now abandoned, which is a continuation-in-part of prior application U.S. Ser. No. 07/500,299 filed Mar. 12, 1990, now abandoned.

FIELD OF THE INVENTION

This invention is in the field of assay devices, including devices for ligand-receptor methods which are used for the detection of selected analytes in a fluid sample. More particularly, this invention relates to devices for performing solid-phase assays requiring a separation of bound from unbound labeled reagents. The inventive devices described herein may be used in the performance of assays to obtain qualitative, semi-quantitative or quantitative determinations of one or more analytes within a single test format.

BACKGROUND OF THE INVENTION

As used herein, the term "ligand-receptor" assay refers to an assay for an analyte which may be detected by the formation of a complex between a ligand and another substance capable of specific interaction with that ligand, i.e., ligand receptor. The ligand may be the analyte itself or a substance which, if detected, can be used to infer the presence of the analyte in a sample. In the context of the present invention, the term "ligand", includes haptens, hormones, antigens, antibodies, deoxyribonucleic acid (DNA), ribonucleic acids (RNA), metabolites of the aforementioned materials and other substances of either natural or synthetic origin which may be of diagnostic interest and have a specific binding partner therefor, i.e., the ligand receptor in the ligand-receptor assay. The term "ligand receptor" includes materials for which there is a specific binding partner, i.e., the ligand of the ligand-receptor assay. Those skilled in the art will appreciate that the analyte of interest, a member of a specific binding pair, may be either ligand or ligand receptor depending upon assay design.

Ligand-receptor assays are generally useful for the in-vitro determination of the presence and/or concentration of ligands in body fluids, food products, and environmental samples. For example, the determination of specific hormones, proteins, therapeutic drugs, and toxins in human body fluids has significantly improved the ability of medical practice to diagnose and minister to the human condition. There is a continuing need for simple, rapid, non-instrumental assays for the qualitative and semi-quantitative determination of such ligands in a sample. This need for simple, rapid methods entails a concomitant requirement for assay devices to complement such assay methods. Furthermore, in many situations, such assays methods need to be simple enough to be performed and interpreted by non-technical users without the requirement of costly and complex apparatus suitable for use only in a laboratory setting by highly skilled personnel.

Ligand-receptor assays rely on the binding of ligands by receptors to determine the concentration of ligands in a sample. Ligand-receptor assays can be characterized as either competitive or non-competitive. Non-competitive assays generally utilize receptors in substantial excess over the amount of ligand to be determined. Sandwich assays, in which the ligand is detected by binding to two receptors, one receptor labeled to permit detection and a second receptor typically bound to a solid phase to facilitate separation of bound from unbound reagents, such as unbound labeled first receptor, are examples of noncompetitive ligand-receptor assays. Proteins, hormones and deoxyribonucleic acid (DNA) are examples of ligands commonly detected using non-competitive assays. Competitive assays generally involve ligand from the sample, a ligand analogue labeled to permit detection, and the competition of these species for a limited number of ligand receptor binding sites. Examples of ligands which are commonly measured by competitive ligand-receptor assays include haptens, hormones and proteins. Antibodies that can bind these classes of ligands are frequently used in both non-competitive and competitive assays as the ligand receptors.

Ligand-receptor assays can be further described as being either homogeneous or heterogeneous. In homogeneous assays, all of the reactants participating in the reaction are admixed and the quantity of ligand is determined by its effect on the binding events involving the labeled species. The signal observed is modulated by the extent of this binding and can be related to the amount of ligand in the sample. U.S. Pat. No. 3,817,837 describes such a homogeneous, competitive immunoassay in which the labeled ligand analogue is a ligand-enzyme conjugate and the ligand receptor is an antibody capable of binding to either the ligand or the ligand analogue. The binding of the antibody to the ligand-enzyme conjugate decreases the activity of the enzyme relative to the activity observed when the ligand-enzyme conjugate is in the unbound state. Due to competition between unbound ligand and ligand-enzyme conjugate for antibody binding sites, as the ligand concentration increases the amount of free ligand-enzyme conjugate increases and thereby increases the observed signal. The product of the enzyme reaction may then be measured kinetically using a spectrophotometer.

Heterogeneous ligand-receptor assays require a separation of bound labeled ligand receptor or labeled ligand analogue from the free labeled ligand receptor or labeled ligand analogue and a subsequent measurement of either the bound or the free fraction. Methods for performing such heterogeneous, competitive assays are described in U.S. Pat. Nos. 3,654,090, 4,298,685, and 4,506,009; such a non-competitive assay is described in U.S. Pat. No. 4,376,110.

The need for ligand-receptor assays that can be performed without the use of instrumentation has led to the development of assay devices that can be visually interpreted. U.S. Pat. Nos. 4,125,372, 4,200,690, 4,246,339, 4,366,241, 4,446,232, 4,477,576, 4,496,654, 4,632,901, 4,727,019, and 4,740,468 describe devices and methods for heterogeneous, ligand-receptor assays that can develop colored responses to permit visual interpretation of the results.

Among the first devices developed for ligand-receptor assays were simple dipstick type devices designed for contacting a porous material such as a membrane with both the sample and labeled reagents via immersion allowing appropriate reagent incubations to occur and then separating the free from the bound label using a wash step. Such devices are described in U.S. Pat. Nos. 3,715,192, 4,200,690, and 4,168,146 and EPO Appl. Nos. 0 032 286 and 0 063 810. A common distinguishing feature of devices constructed in a dipstick format is the absence of a fluid receiving zone within the device for containing the sample, liquid reagents and wash solutions after the performance of the sample and reagent incubations and the separation of free from bound label. The lack of such a fluid receiving zone precludes characterization of such a dipstick device as self-contained, given that some external fluid receptor must be provided to capture used sample, unbound labeled reagents and spent wash fluid.

A class of devices which constitute an improvement over the simple dipstick construct is the immunochromatographic test strip device. This class of device generally exhibits improved sensitivity in ligand detection relative to that of simple dipstick devices by virtue of the ligand concentrating effect achieved by the flow of sample containing the ligand past an immobilized ligand receptor zone. Such devices also provide a limited fluid receiving zone for fluids used in the performance of the assay. A fluid receiving zone is created by increasing the length of the porous member to provide a suitable amount of total void volume capacity. Such devices are described in U.S. Pat. Nos. 4,094,647, 4,235,601, 4,361,537, 4,366,241, 4,435,504, 4,624,929, 4,740,468, 4,756,828, and 4,757,004; EPO. Appl. Nos. 0 267 006, 0 271 204, and 0 299 428; and PCT Appl. No. US86/0668. Even though such immunochromatographic devices do include a limited fluid receiving zone, they do not enable an efficient free/bound label separation, since the rate of separation is slow and limited by the rate at which fluid travels along the length of the porous member. Some immunochromatographic devices are so limited by the capacity of their fluid zone that no free/bound label separation can be performed; such devices rely upon the increase in concentration of label at the immobilized ligand receptor zone to distinguish bound from free label. A need exists for a device that is both efficient and rapid in performing separation of the free from the bound label in an assay.

A specialized form of an immunochromatographic device is employed in the method of radial partition immunoassay. In this assay method, the sample and labeled reagents are carefully applied to the immobilized receptor zone in the center of the porous material. The wash fluid is then also carefully applied to the immobilized receptor zone and the unbound label flows radially away from the central immobilized receptor zone. Radial partition immunoassay devices like the aforementioned immunochromatographic devices require that the volume of wash fluid be less than the total void volume of the porous member containing the ligand receptor since it is the void volume of the porous member in excess of the volume of the sample which provides the necessary additional fluid capacity. Such radial partition immunoassay devices are described in U.S. Pat. Nos. 4,517,288, 4,670,381, 4,752,562, 4,774,174, and 4,786,606. Devices used for radial partition immunoassay are not generally suitable for the detection of a multiplicity of ligands. The usable ligand detection zone necessarily must be relatively small and constrained since the physical separation of free and bound labeled species is strictly limited by the dimensions of the device and the total fluid capacity of the porous member.

Immunochromatographic and radial partition immunoassay devices depend primarily on horizontal separation, i.e., along or within the plane of the porous member, of the free and bound labeled species in order to achieve acceptable physical separation of the free from the bound labeled reagents. A separate class of devices utilizes flow of fluid in a direction which is primarily transverse to the plane of the porous member. Devices which operate in this manner may be generally referred to as "flow-through" devices. The absorbent material which constitutes the fluid receiving zone in these devices can either be in non-continuous contact with the porous member containing immobilized receptor as described in U.S. Pat. Nos. 3,888,629 and 4,246,339 or in continuous contact with the porous member as described in U.S. Pat. Nos. 4,366,241, 4,446,232, 4,632,901 and 4,727,019, and in EPO. Appl. No. 0 281 201. Devices in which the absorber is not in continuous contact with the porous member such as described in U.S. Pat. Nos. 3,888,629 and 4,246,339 allow the contact of the solutions containing sample and/or labeled reagents with the porous member to occur prior to permitting flow of the labeled reagent solution into the fluid absorbent. Since the contact is not continuous between the absorber and the porous member, the volume of fluid needed to ensure that the porous member is completely saturated is only the void volume of the porous member. Such non-continuous contact devices are inherently more efficient at utilization of sample and labeled reagents and thus by this measure are more cost-effective than are continuous contact flow-through devices such as those described in U.S. Pat. Nos. 4,446,232, 4,632,901 and 4,727,019. The non-continuous contact flow-through devices however, have the disadvantage that a physical motion is required by the assayist to bring the separated absorber into contact with the porous member and to thereby enable the flow of fluid needed for separation of free label from bound label. The requirement of direct mechanical intervention is not desirable from the perspective of ease of use by non-trained users, as it introduces a step which may be subject to error. The continuous contact flow-through devices eliminate the need for active intercession by the user to complete the fluid contact between the absorber and the porous member, but are less efficient in the utilization of costly labeled reagents. The flow characteristics of such devices are optimized such that fluid flow in the direction transverse to the plane of the porous member is preferred. Thus, a reagent volume substantially greater than the void volume of the porous member is required to ensure that the entire porous member has been contacted with the solution containing reagents. Since neither the non-continuous nor the continuous contact flow-through devices described in the prior art are capable of providing a device which exhibits the characteristics both of efficient use of labeled reagents and of avoiding the need for an additional mechanical intercession step, there remains an unmet need for a device with such attributes.

The inventive devices herein described are not limited to either a flow through or an immunochromatographic method but rather may be modified to achieve the benefits of both by, for example, controlling the placement of the sample or the design and placement of the porous and non-absorbent members. In preferred embodiments reagent flow is primarily tangential to the porous membrane while washing reagent flow is primarily transverse to the membrane and then into the network of capillary channels. These features distinguish this invention over the flow through and immunochromatographic devices of the prior art.

Control of the rate and path of fluid flow in an assay device can be of paramount importance. To achieve this end, a number of devices have been described in the prior art which use surfaces with specifically arranged geometric elements to control the path and the rate of fluid flow. Devices such as are described in U.S. Pat. Nos. 3,690,836 and 4,426,451 and EPO. Appl. No. 0 034 049 utilize an arrangement in which a porous member is placed between smooth surfaced planar sheets of a non-absorbent material in order to contain a fluid within the porous material. Devices such as are described in U.S. Pat. Nos. 4,233,029 and 4,310,399 use geometric arrangements of capillary channels to modulate the flow of fluid, such that fluid is directed to flow in regular geometric patterns and at controlled rates. A device for controlling the delivery of fluid a porous member using a textured surface possessing a surface capillary network is described in EPO. Appl. No. 0 239 174. while the devices described are suitable for control of fluid flow, they fail to control fluid flow through a porous member such that assay devices can be constructed to make efficient use of sample and labeled reagents and to contain a suitable fluid receiving zone for use in achieving a rapid and efficient separation of free from bound labeled species in an assay. Thus remains a need which has been unmet by any of the aforementioned architecture-controlled flow devices.

A preferred device for performing ligand-receptor assays should not impose the need for mechanical intercession on the assay procedure because this may introduce operator error. The inventive devices herein described and claimed are efficient in their use of sample and costly reagents and provide an adequate fluid receiving zone for all liquid reagents, particularly those of the free/bound separation step in an assay. The devices are capable of supporting ligand-receptor assays directed to simultaneous detection of a multiplicity of target ligands and they may be used in ligand-receptor assay formats which are analogous both to those of flow-through assays and to those of immunochromatographic assays.

One advantage of the devices herein described is the efficient use of reagents while incurring a minimum number of steps in the assay protocol. The device allows one to use a large porous membrane and to cover it with multiple ligand receptor zones, because it ensures that the sample will flow over and cover the entire membrane. This is accomplished without the need for either large sample volumes or mechanical action. Another advantage of this invention is the non-absorbent member. When an excess volume of fluid is added, the network of capillary channels formed by the contact of the porous member and the nonabsorbent member ensures washing efficiency by directing flow away from the porous member, thereby assuring good separation of free from bound labeled conjugate. In one embodiment the inventive device can be employed in assays using flow-through methods. In another embodiment the described device can perform assays using immunochromatographic methods. Further, the device of the present invention efficiently performs the task of separating free labeled species from bound labeled species, a pivotal requirement for heterogeneous ligand-receptor assay methods.

SUMMARY OF THE INVENTION

The present invention is directed to an apparatus particularly useful for performing a ligand-receptor assay in which it is necessary to separate free from bound labeled reagents. In general, the devices are useful in situations where it is desirable to remove label not complexed to immobilized binding agent from label which is complexed to binding agent. The apparatus of the present invention includes, a porous member such as a membrane or a filter onto which may be bound a multiplicity of binding agents, such as an antibody, preferably a monoclonal antibody against the target ligand (FIGS. 1 and 2). The apparatus also includes a nonabsorbent member with a textured surface in communication with the lower surface of the porous member. The textured surface of the nonabsorbent member may be a grooved surface such as the surface of a record or it may be composed of channels, such that when the porous and nonabsorbent members are brought into contact with one another a network of capillary channels is formed. The capillary network is formed from the contact of the porous member and the textured surface of the nonabsorbent member and can be constructed either before or subsequent to the initial contacting of the porous member with a fluid. This is not meant to imply that actual physical contact between the porous member and the textured surface of the nonabsorbent member is required. The porous member and the textured surface of the nonabsorbent member are in fluid communication. That is to say that when fluid is added to the device, fluids are drawn through the porous member by at least one capillary which has been formed by the fluid communication between these two members. The capillary network may include capillaries formed from the contact of the outer surface of the porous member with the open channels of the nonabsorbent member. The upper and lower surfaces of the porous member may, but need not be, of the same composition, the upper and lower surfaces of the porous member refer to different areas of the same material. Generally, the upper and lower surfaces of the porous material are of similar shape and dimension and are the planar exposed portions of a porous member. In some embodiments, the capillary communication between the porous member and the nonabsorbent member favors delaying the transferral of fluid from the porous member to the capillary network formed by the porous member and the textured surface of the nonabsorbent member until the volume of the added fluid substantially exceeds the void volume of the porous member. The transferral of fluid from the porous member to the network of capillary channels formed by the porous member and the textured surface of the nonabsorbent member, occurs without the use of external means to induce fluid transference including but not limited to positive external pressure, vacuum, or contact with an absorbent material. The devices of the present invention may also include an optional member which is placed in contact with the upper surface of the porous member and may be used to partition the upper surface of the device into discrete openings. Such openings can access either the porous member or the textured surface of the nonabsorbent second member. The optional member can in conjunction with the nonabsorbent member compose a fluid receiving zone in which there is no intervening porous member. A fluid receiving zone constructed from the nonabsorbent member and the optional member provides fluid capacity in addition to that provided by the network of capillary channels created by the contact of the porous member and the nonabsorbent member. The openings in the optional member may include a first fluid opening and also an additional fluid opening. The first fluid opening functions as a portal for the introduction of the first fluid added to the device. The additional fluid opening serves as an additional portal through which additional fluids may be added to the inventive device.

The first fluid added to the device is the sample. Depending on the structure of the assay protocol, the sample may include but is not limited to sample-derived target ligand, labeled ligand analogue conjugate, labeled ligand receptor conjugate, ligand receptor, binding agent, free/bound label separation reagents and/or elements of the signal development system. Additional fluids added to the device may contain the remaining reagents necessary to complete the assay procedure. Additional fluid reagents depending on the assay protocol may include but are not limited to specimen-derived target ligand, labeled ligand analogue conjugate, labeled ligand receptor conjugate, ligand receptor, binding agent, free/bound separation reagents and/or elements of the signal development system. Depending on the structure of the assay protocol several additional fluid reagents may be needed to complete the assay procedure with the composition of successive additional fluid reagents varied as appropriate to the assay protocol.

An assay using the devices of this invention comprises in part the steps of adding a volume of the sample to the porous member, where the sample permeates the void volume of the porous member and thereby contacts the ligand receptor immobilized on the porous member. In a non-competitive ligand receptor assay the sample containing a target ligand is applied to the porous member and the target ligand is bound by the ligand receptor which is non-diffusively immobilized on the porous member. Labeled second ligand receptor is then added as an additional fluid and binds to the complex of ligand and immobilized first ligand receptor. Alternatively labeled second ligand receptor can be combined with the target ligand to form the sample prior to application of the sample to the porous member so that the binding of labeled second ligand receptor to target ligand occurs prior to the binding of target ligand to first ligand receptor immobilized on the porous member. Alternatively, the target ligand, labeled second ligand receptor and first ligand receptor are combined and the complex of first ligand receptor/target ligand/labeled second ligand receptor binds to a binding agent that is either combined with these reagents or is immobilized on the porous member. An additional fluid containing reagents to effect a separation of free from bound labeled reagents may be added to remove excess ligand and excess labeled second ligand receptor, if needed. This device is designed to provide sufficient sensitivity to measure low concentrations of target ligand because one can use large amounts of sample and efficiently remove the excess of either or both target ligand and labeled second ligand receptor. Indeed, the efficient separation of free from bound label achieved by the network of capillary channels of this device improves the discrimination of specific ligand associated signal over non-specific background signal. If needed, a signal developer solution is then added to enable the label of the labeled second ligand receptor to develop a detectable signal. The signal developed may then be related to the concentration of the target ligand within the sample. In a preferred embodiment, the transfer of fluid between the porous first member of the device and the network of capillary channels formed by the contact of the porous member and textured surface of the nonabsorbent second member of the device is generally self-initiated at the point when the total volume of fluid added to the device exceeds the void volume of the porous member, thus obviating the need for active interaction by the user to remove excess fluid from the analyte detection zone. The-point at which the fluid transfer is initiated is dependent upon the objectives of the assay. Normally, it is desirable to contact the sample with all of the zones on the porous member which contain immobilized receptor so that the application of additional fluid effects the separation of unbound label from label which has bound to the porous member.

A competitive ligand receptor assay may be performed using the devices of the present invention by adding a sample containing the target ligand and labeled ligand analogue conjugate to ligand receptor immobilized on the porous member. Labeled ligand analogue conjugate and target ligand compete for the binding sites of the ligand receptor. Alternatively, ligand receptor may be combined with target ligand and labeled ligand analogue with subsequent immobilization of ligand receptor onto the porous member through contact with a binding agent. An additional fluid to separate the free from bound label may be added to the device, followed if needed by a signal development solution to enable detection of the label of the labeled ligand analogue conjugate which has complexed with ligand receptor immobilized on the porous member. The amount of labeled ligand analogue conjugate bound to the porous member is related to the concentration of target ligand in the sample. The fluid transfer between the porous member and the network of capillary channels formed by the contact of the porous member and the textured surface of the nonabsorbent second member is generally self-initiated when substantially all the void volume of the porous member has been filled with fluid. The method of the present invention thereby enables the detection of analytes in a manner which is simple, rapid, convenient, sensitive and efficient in the use of labeled reagents.

The devices of this invention may simultaneously detect multiple binding agents. The surface (normally the upper surface) of the porous member may be considered to be composed of a large number of unitary surface area elements. Each detectably distinguishable surface area element is capable of supporting a reaction which is independent of the reactions occurring at neighboring surface area elements. As used herein, "reaction" is a broad term which includes mechanical filtration effects. The determination of what constitutes an independent surface area element is largely determined by one's ability to attach binding agents to the surface of the porous member, as well as the spatial resolution of the signal detection mechanism. For example, in a visually detected assay, it is quite possible to deposit and subsequently visualize a reagent spot of about 1 $mm^2$ in area. On a porous member with surface dimensions of only 0.1 in.×1.2 in. (i.e., a surface area of approximately 77 $mm^2$) it would not be possible to have more than 30–40 of such reaction zones detectable by the human eye. The binding agent may physically or chemically (which includes immunological means) bind target ligands to the porous member. Physical binding agents include diffusible microparticles which are filtered out of sample/reagent solutions. Chemical binding agents include ligand receptors such as antibodies capable of immunologically binding to target ligands. Clearly, a multitude of simultaneous, independent reactions may be detected using these devices.

The devices of this invention may be used to perform either flow-through assay methods or immunochromatographic assay methods by controlling the relative fluid retentive properties of the porous and non-porous members.

In flow-through assay methods the device can, by proper control of relative fluid retentive properties of the porous member and the nonabsorbent textured surface member, be made to operate such that the porous member must be completely saturated with reaction fluid prior to transfer of fluid from the porous member to the nonabsorbent member. This property is advantageous since the ability to utilize a minimum of reaction fluids results in the most efficient use of liquid reagents.

DEFINITIONS

Figure 1:
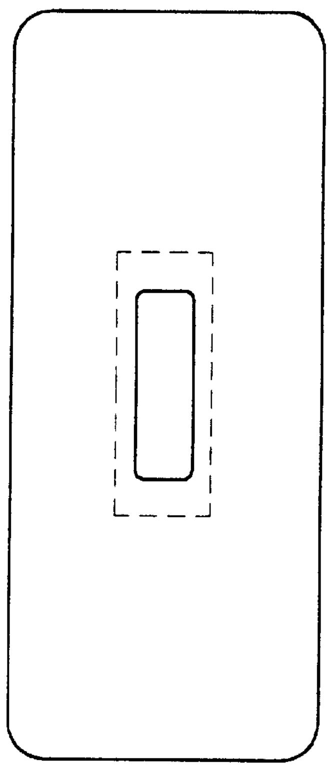
FIG. 1 is an enlarged top view of an apparatus for performing an immunoassay in accordance with the present invention.
Figure 2:
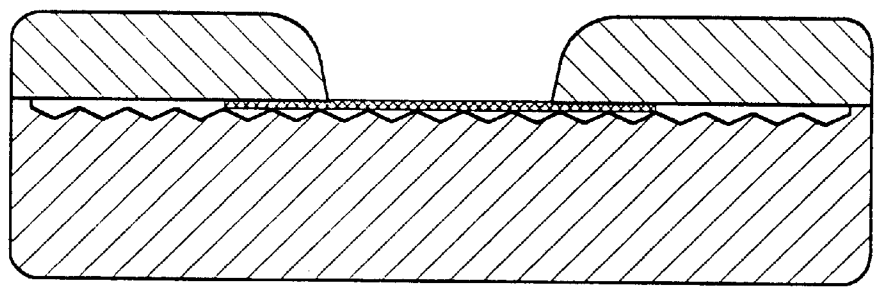
FIG. 2 is a section view, on an enlarged scale, of the apparatus represented in FIG. 1.

As used throughout, the following terms shall be defined:

Binding Agent: a substance which is capable of binding by chemical, physical or immunological means to the ligand of diagnostic interest or a ligand receptor therefor.

Porous Member: a member of the device composed of a porous material used to provide the solid phase support for the binding agent.

Void Volume: the volume of space within the porous member that can be occupied by fluid.

Fluid Retentive Forces: forces which retain fluid within the void volume of the porous member, e.g. surface tension.

Channel: an open groove of capillary dimensions (generally less than 0.20 of an inch).

Capillary Channels: enclosed channel of capillary dimensions (generally less than 0.20 of an inch).

Set of Channels: a group of channels identifiable by a set of common characteristics, e.g., alignment along a common device axis.

Network of Capillary Channels: a pattern of capillary channels formed by the contact of the porous member and the channels of the textured surface of the nonabsorbent member, networks may be constructed from one or more sets of channels.

Textured Surface: nonabsorbent surface capable of forming a network of capillary channels when the porous membrane is positioned above it. The textured surface may be randomly or regularly patterned.

Textured Surface Nonabsorbent Member: a member which does not absorb fluid and contains the textured surface on a portion of its surface. Contact between the textured surface of the nonabsorbent member and the porous member forms the network of capillary channels.

Optional Member: an additional member which when included in the device permits the upper surface of the device to be partitioned into discrete openings.

First Fluid Opening: an opening in the optional member to permit the introduction of the sample into the device.

Additional Fluid Opening: an additional opening in the optional member to permit the introduction of additional fluids to the device.

Sample: the first volume of fluid added to the device which may include but is not limited to specimen-derived target ligand, labeled ligand analogue conjugate, labeled ligand receptor conjugate, ligand receptor, binding agent, free/bound label separation reagents and/or elements of the signal development system.

Additional Fluid: any additional fluid which must be added to the device to complete the assay protocol including but not limited to specimen-derived target ligand, labeled ligand analogue conjugate, labeled ligand receptor conjugate, ligand receptor, binding agent, free/bound label separation reagents and/or elements of the signal development system.

The inventive devices herein described may be used in a variety of assay formats, including those described in U.S. Pat. Nos. 5,028,535 and 5,089,391 filed Jan. 10, 1989 and which is hereby incorporated by reference. In particular, as used in the method claims of this application, the definitions of "ligand," "ligand receptor," "ligand receptor conjugate" and "ligand analogue conjugate" are incorporated by reference from U.S. Pat. Nos. 5,028,535 and 5,089,391.

DETAILED DESCRIPTION OF THE PREFERRED EMBODIMENTS

The device of the present invention uses a porous member constructed of a porous material such as a membrane or filter. Preferred for use as porous members are filters or membranes which comprise, in part, materials which can allow fluid to enter the void volume of the porous material. The void volume of the porous material is the volume contained within the dimensional limits of the material which may be occupied by fluid. It also should be noted that these inventive devices may be used with a variety of fluids, including liquids and gases.

In a preferred embodiment of the device, substantially all of the sample is retained within the confines of the porous member prior to fully saturating the void volume of the porous member. By retaining the sample added to the device within the porous membrane until such time as the void volume of the porous membrane is substantially filled, only a minimum volume of sample is required so as to ensure that the entirety of the membrane activated with binding agent has been exposed to the added sample. This results in the most efficient use of added sample for simultaneously conducting a multiplicity of target ligand detection reactions upon the membrane. Materials which may therefore be used as the porous member include materials in which there are operative forces which retain fluid within the material, i.e. fluid retentive forces. Particularly preferred for use as porous members are materials in which the fluid retentive forces exerted by the porous member on retained fluid are such that substantially all the void volume of the porous material is filled prior to substantial fluid transfer between the porous member and the network of capillary channels created by the contact of the porous member with the textured surface nonabsorbent member. Membranes or filters which may be used include those constructed of glass fibers and various synthetic and natural materials.

A preferred method for achieving the appropriate fluid retentive properties within the porous member is the selection of a membrane, characterized by a pore size, such that the fluid retentive forces exerted by the membrane are greater than the external forces active on the fluid within the membrane. Examples of such external forces are the pressure of fluid above the membrane (fluid head pressure), gravitational forces on fluid within the membrane, the relative degree to which the material may be characterized as hydrophilic and the capillary forces associated with external capillaries or networks of capillaries which are in contact with the membrane. Pore sizes for membranes such as nylon membranes, preferred for use as porous members are in the range of 0.1 to 30 $\mu$m, particularly preferred for use are membranes with pore sizes in the range of 0.2 to 5 $\mu$m. When an assay process does not require the saturation of substantially all of the void volume of the porous member prior to fluid transfer, porous materials exhibiting fluid retentive forces that are less than or equal to the external forces active on the fluid within the porous member may be used. Under these circumstances porous members such as membranes with pore sizes in the range of 5 to 50 $\mu$m are preferred.

Target ligand is captured upon the porous member. The capture process may utilize physical entrapment such as would occur during filtration in which the target ligand is of a size greater than the pore size which characterizes the porous member or may occur from the interaction of an agent, i.e. a binding agent, which is capable of binding to the target ligand or the ligand receptor therefor. A binding agent such as a ligand receptor may be directly or indirectly bound to the porous member. A ligand receptor, for example an antibody, may be nondiffusively immobilized on the porous member. In a preferred embodiment, the porous member is a membrane such as a nylon membrane upon which ligand receptor is immobilized, a preferred ligand receptor is an antibody. The antibody may be from a polyclonal antibody preparation, though a preferred antibody is a murine monoclonal antibody. The methods for preparation and screening of suitable such murine monoclonal antibodies are well known to those skilled in the art, see for example, Liu, D. Purssell, R. and Levy, J. G., *Clinical Toxicology,* 25, 527–538 (1987). The murine monoclonal antibody is nondiffusively immobilized on the membrane either by covalent or non-covalent methods, such methods also are well known to those skilled in the art, see for example, Pluskal, M. G., Przekop, M. B., Kavonian, M. R., Vecoli, D., Hicks, D. A., *BioTechniques,* 4, 272–283 (1986). In a preferred embodiment the murine monoclonal antibody is noncovalently bound to a nylon membrane. In a particularly preferred embodiment, the monoclonal antibody is noncovalently immobilized in a discrete zone on the nylon membrane. Immobilization of a monoclonal antibody in a discrete zone on the membrane composing the porous member is particularly preferred since this permits the surface of the membrane to be partitioned into a multiplicity of such discrete zones of immobilized antibody, the different zones containing the same or different antibodies. Each discrete antibody zone may be used to complete a discrete immunochemical reaction and thereby a number of such immunochemical reactions may be performed simultaneously.

In a preferred embodiment of the present invention the binding agent, a ligand receptor, is immobilized substantially uniformly in a single zone which encompasses the entirety of the porous member. In a further preferred embodiment, the ligand receptor is immobilized in at least one discrete zone upon the porous member so that any such discrete zone embodies less than the entirety of the porous member. In a particularly preferred embodiment, the ligand receptor is immobilized uniformly within one or more discrete zones. In a further particularly preferred embodiment, a multiplicity of ligand receptors are immobilized in a multiplicity of discrete zones, each zone containing at least one ligand receptor. In a further particularly preferred embodiment, the multiplicity of discrete zones is at least as great as the multiplicity of target ligands to be determined. When a multiplicity of discrete ligand receptor zones are present, the determination of a multiplicity of ligands is then enabled.

The second element of the present invention is a nonabsorbent construct having a surface texture which, when in contact with the porous member comprises in part a network of capillary channels. The surface texture can be composed of either regular or irregular geometric elements disposed in such a manner to provide channels. Sets of channels are formed when a group of channels may be characterized by common features such as alignment along a single axis. The channels form a network of capillary channels when the nonabsorbent member is in contact with the porous member. The network of capillary channels may be beneath or around the porous membrane. The communication between porous and nonabsorbent members is such that when the fluid volume added to the porous member is greater than the void volume of the porous member, fluid is transferred from the porous member to the network of capillary channels formed by the contact of the porous and nonabsorbent members. Under some circumstances, the fluid retentive properties of the porous member permit such fluid transfer before the void volume of the porous member is substantially saturated. The porous member may be disposed relative to the nonabsorbent member such that a network of capillary channels is formed where the two members are in contact and the adjacent surfaces of the two members are generally parallel. This includes, for example, two curved surfaces which are substantially parallel throughout the curvature. So long as the two surfaces do not get so far apart so that the gap between them becomes greater than a capillary distance, it is only required that the two surfaces be substantially parallel. The surfaces need not be co-planar or flat. The textured surfaces may be planar or non-planar. The distance separating the porous member and the textured surface of the nonabsorbent member is such that the surface of the porous member adjacent to the textured surface of the second member completes the formation of a network of capillary channels between the two members. Indeed, in assay protocols in which additional fluids are introduced, the porous and nonabsorbent members may not have to be brought into intimate contact at all, provided that the volume of fluid used is sufficient to substantially fill the void volume of the porous member and provided that the porous and nonabsorbent members are disposed a distance relative to one another so that the channels of the nonabsorbent member are still able to fulfill the function of a fluid receiving zone as intended. Preferred as distances separating the porous member and the textured surface of the nonabsorbent member are distances less than 0.2 inch. Particularly preferred as separation distances between the two members forming the network of capillary channels are distances of less than 0.1 inch.

Figure 3:
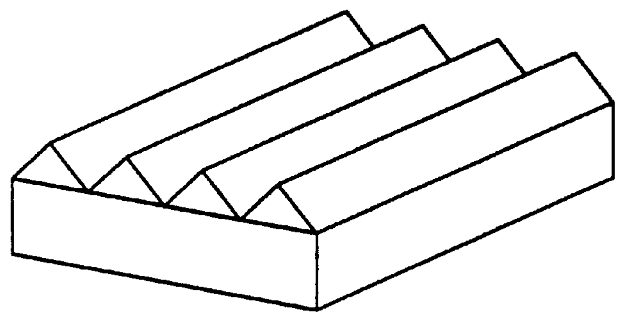
FIG. 3 is an enlarged perspective view of a textured surface with a single set of linear channels.
Figure 4:
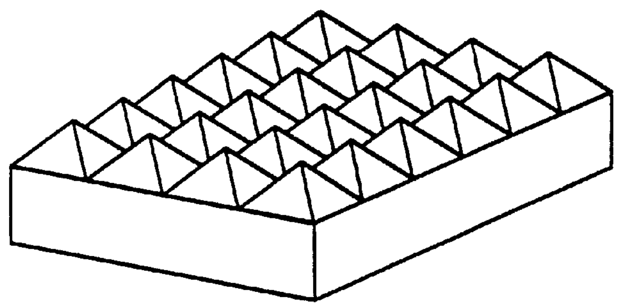
FIG. 4 is an enlarged perspective view of a textured surface composed of two sets of channels with equal channel widths.
Figure 5:
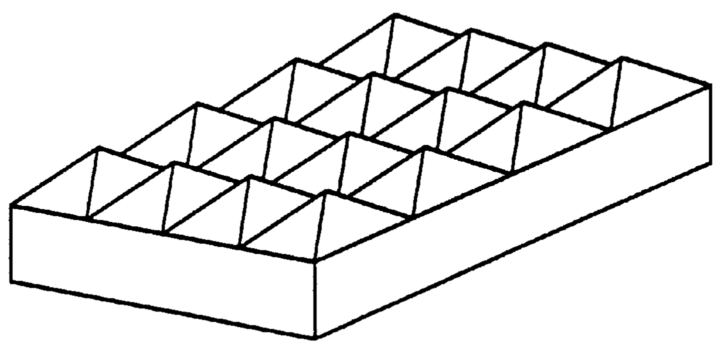
FIG. 5 is an enlarged perspective view of a textured surface composed of two sets of channels with dissimilar channel widths.

In a preferred embodiment of the nonabsorbent member, the textured surface is comprised of sets of channels forming regular geometric patterns; the channels being generally aligned along a single axis and adjoining channels being generally parallel (FIG. 3). Within the preferred embodiment of the textured surface, fluids are generally caused to flow along the channels similar to the description of such flow as described in U.S. Pat. No. 4,233,029, incorporated by reference herein. In a particularly preferred embodiment of the second member, the textured surface is comprised of a regular geometric pattern in which two sets of channels are juxtaposed at an angle upon the surface of the member, each set of channels being generally aligned along its respective single axis, with adjoining channels along a single axis being generally parallel. A preferred angle for the juxtaposition is such that the two sets of channels are not collinear. Particularly preferred as an angle for the juxtaposition of the two sets of channels is an angle substantially equal to a right angle (i.e., 90°). In a preferred embodiment of a textured surface in which the channels are juxtaposed at a right angle, the channels are of generally the same width so that the geometric pattern created by the two sets of channels is that of a pattern of squares (FIG. 4). In a particularly preferred embodiment of a textured surface in which the two sets of channels are at right angles to one another, the channels are of generally dissimilar widths such that the two sets of channels form a pattern that is a pattern of rectangles (FIG. 5). The preferential direction of flow in the anisotropic rectangular array is generally first along the axis parallel to the axis defined by the wider channels and secondarily along the axis parallel to the axis defined by the narrower channels. Our research shows that the fluid flow patterns for single plates comprised of two sets of channels juxtaposed at right angles to one another are similar to the fluid flow patterns described for systems composed of two generally parallel plates each of which is comprised of a single set of channels and with such plates opposed a distance apart so as to thereby construct a two-dimensional arrangement of channels. The flow patterns of such two-dimensional arrangements of channels are described in the aforementioned U.S. Pat. No. 4,233,029, incorporated by reference herein.

The third element of the inventive device is comprised of a nonabsorbent optional member. The nonabsorbent optional member is placed over the upper surface of the porous member. The nonabsorbent optional member may have openings through which fluids are added to the porous member. The openings in the optional member serve to partition the upper surface of the porous member into zones onto which fluids may be selectively introduced as appropriate to the specific assay protocol. The first fluid opening is used to introduce sample onto the porous member. If appropriate to the assay protocol, such as in a flow-through type assay, subsequent fluid additions such, as a free/bound label separation fluid, may be added through the first fluid opening. A second fluid opening may be included in the optional member if required by the assay protocol, such as in an immunochromatographic assay, to permit the introduction of additional fluids, such as fluids containing elements of the signal development system, onto portions of the porous member separate from the location at which sample is introduced. The nonabsorbent optional member may optionally include a textured surface similar in nature to that of the textured surface nonabsorbent member. The third element in combination with the nonabsorbent member also may form a chamber containing the porous member. In cases where the sample is a gas, the gas may be injected into the chamber containing the porous member such that the sample is passed over and through the porous member and out of the chamber.

The network of capillary channels formed by the contact of the porous member and the textured surface of the textured surface nonabsorbent member serves as the primary fluid reservoir of the inventive device. Additional fluid reservoir capacity can be provided by space within the inventive device enclosed by the combination of the textured surface nonabsorbent member and the nonabsorbent optional member. In a preferred embodiment of the inventive device the additional fluid reservoir capacity is provided by the space enclosed by the textured surface nonabsorbent member and the nonabsorbent optional member and where within such an enclosed space there is no porous member intervening between the two nonabsorbent members.

Figure 6:
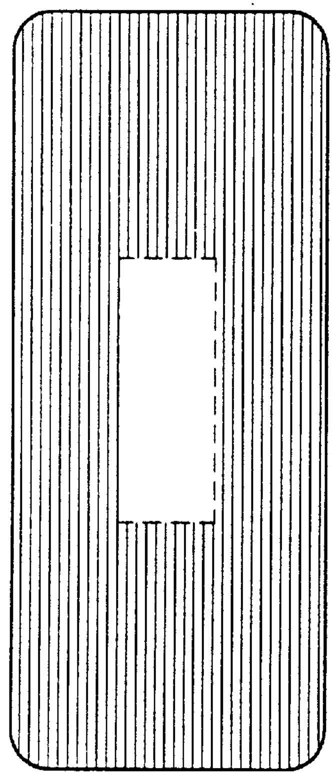
FIG. 6 is an enlarged top view of a device with a porous member over a textured surface nonabsorbent member.
Figure 7:
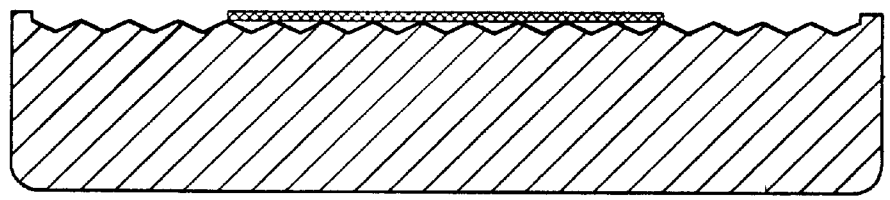
FIG. 7 is a section view, on an enlarged scale, of the device represented in FIG. 6.

In a preferred embodiment of the inventive device, the device comprises in part a porous member and a textured surface nonabsorbent member (FIG. 6 and 7). In a particularly preferred embodiment of the inventive device, the device comprises in part a porous member, a textured surface nonabsorbent member and a nonabsorbent optional member with a first fluid opening over the medial portion of the porous member. Sample is introduced onto the portion of the porous member exposed by the first fluid opening in the nonabsorbent optional member. Once introduced, the sample is allowed to spread or wick over and into the porous member and is thereby induced to interact with ligand receptor which is non-diffusively immobilized upon the porous member. The nonabsorbent member of the inventive device includes a textured surface comprising sets of channels. The sets of channels form a network of capillary channels when the nonabsorbent member is brought into contact with the porous member. Such contact may be initiated before or subsequent to the initial sample introduction step. The network of capillary channels formed by the contact of the porous member with the nonabsorbent member provides a fluid receiving zone into which fluid may be transferred from the porous member. The network of capillary channels formed between the porous member and the nonabsorbent member is capable of initiating fluid transfer between the porous member and the nonabsorbent member without the need for application of additional external means to induce fluid transfer such as pressure or vacuum.

In a further particularly preferred embodiment, the device of the present invention comprises in part a textured surface nonabsorbent member, a porous member, and a nonabsorbent optional member with a first fluid opening and an additional fluid opening. The first fluid opening is located at an extremity of the porous member. The additional fluid opening is located above the medial portion of the porous member. Sample is added to the device through the first fluid opening and is allowed to spread or wick over and into the porous member and is thereby induced to interact with ligand receptor which is non-diffusively immobilized upon the porous member. Additional fluid as required by the assay protocol is added to the device via the additional fluid opening and then spreads over and into the porous member and thereby completing the assay.

Figure 8:
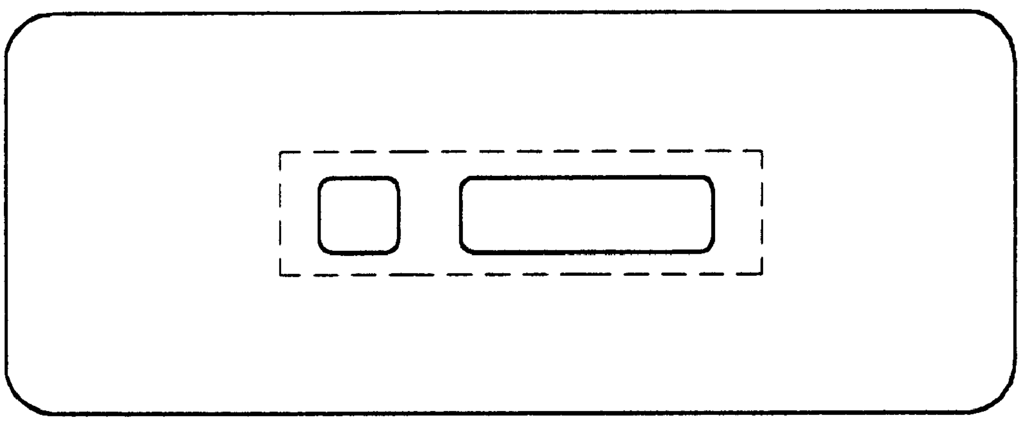
FIG. 8 is an enlarged top view of a device with a porous member between a textured surface nonabsorbent member and an optional member in which the sample is added to the device via a first fluid opening in which the porous member exposed by the first fluid opening cannot form a capillary network with the textured surface of the nonabsorbent second member and an additional fluid opening in which the porous member exposed by the additional fluid opening forms a network of capillary channels with the textured surface of the nonabsorbent member.
Figure 9:
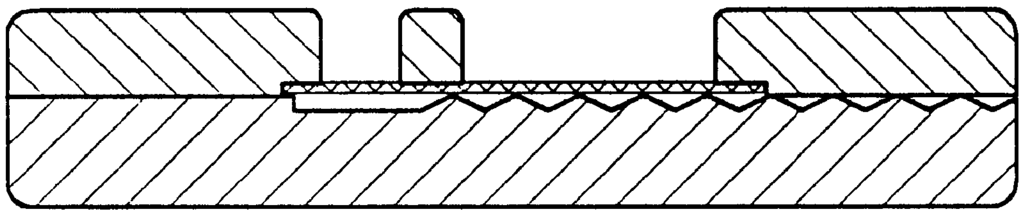
FIG. 9 is a section view, on an enlarged scale, of the device represented in FIG. 8.

In a further preferred embodiment, the device of the present invention comprises in part a textured surface nonabsorbent member and a porous member which, while in contact with the textured surface of the nonabsorbent member includes an extremity of the porous member which extends beyond the perimeter of the textured surface of the nonabsorbent member. In a further particularly preferred embodiment, the device of the present invention comprises in part a textured surface nonabsorbent member, a nonabsorbent optional member with a first fluid opening and an additional fluid opening, and a porous member which, while in contact with the textured surface of the nonabsorbent member includes an extremity of the porous member which extends beyond the perimeter of the textured surface of the nonabsorbent member (FIGS. 8 and 9). The first fluid opening is located above the extremity of the porous member which protrudes beyond the perimeter of the textured surface of the nonabsorbent member. The portion of the porous member which protrudes beyond the perimeter of the textured surface of the nonabsorbent member does not participate in the formation of a network of capillary channels such as is the result of the contact of the porous member and textured surface nonabsorbent members. The first fluid opening is constructed so as to constrain the sample added through the first fluid opening to traverse the porous member and to remain substantially within the confines of the porous member so long as the combined volumes of sample plus additional fluid added do not substantially exceed the void volume of the porous member. In a particularly preferred embodiment of the device the lower surface of the porous member which protrudes beyond the textured surface is sealed so that fluid is unable to pass through that surface. By such constraints upon fluid flow in the porous member, sample added to the first fluid opening is induced to travel within the porous member in a sequential manner, initiating at the porous member below the first fluid opening and progressing to a region of the porous member distal to the first fluid opening. The additional fluid opening is located above the medial portion of the porous member and permits additional fluid to be added to the device as required by the assay protocol. Additional fluid introduced through the additional fluid opening is allowed to spread over the porous member such that flow of such fluids added to the device through the additional fluid opening is not constrained to flow solely within the porous member but may include fluid flow along the outer surface of the porous member. In a further particularly preferred embodiment of the device, the total fluid receiving capacity of the device is increased by the volume associated with the space enclosed by the nonabsorbent member and the optional member in which the porous member does not intrude.

In a further embodiment, the device of the present invention comprises in part a porous member and a textured surface nonabsorbent member with a portion of the textured surface which extends beyond the perimeter of the porous member. In a preferred embodiment, the device comprises in part a porous member, a textured surface nonabsorbent member with an extremity of the textured surface which extends beyond the perimeter of the porous member and an optional member with a first fluid introduction opening located over the portion of the textured surface of the nonabsorbent member which extends beyond the perimeter of the porous member. Sample is added to the device through the first fluid opening in the optional member and is allowed to spread over and along the textured surface underlying the first fluid opening. The extremity of the textured surface of the nonabsorbent member is not overlaid by the porous member so that when the porous member and textured surface of the nonabsorbent members are brought into contact thereby forming a network of capillary channels in the region in which the two members overlap, the extremity of the textured surface does not become part of such a network. The sample added traverses the extremity of the textured surface of the nonabsorbent member originating at the first fluid opening and progressing to the region of the network of capillary channels where the nonabsorbent member is contiguous with the porous first member. Initiating at the juncture where the textured surface of the nonabsorbent member conjointly forms a network of capillary channels due to contact with the porous member, sample flow either along the network of capillary channels or through the porous member is affected by the relative strengths of the fluid retentive forces exerted upon by the sample by the network of capillary channels and by the porous member. With an aqueous sample for example, if the porous member is relatively more fluid retentive than is the network of capillary channels then sample will prefer to flow within the porous member; conversely, if the porous member is relatively less fluid retentive than the network of capillary channels sample flow will occur primarily within the network of capillary channels. Given that the fluid retentive forces favor the retention of sample within the porous member, subsequent to sample flow within the network of capillary channels, sample initially contained within the network of capillary channels is spontaneously transferred from the network of capillary channels to the porous member. The volume of such sample transfer from the network of capillary channels to the porous member is limited by the void volume of the porous member.

Figure 10:
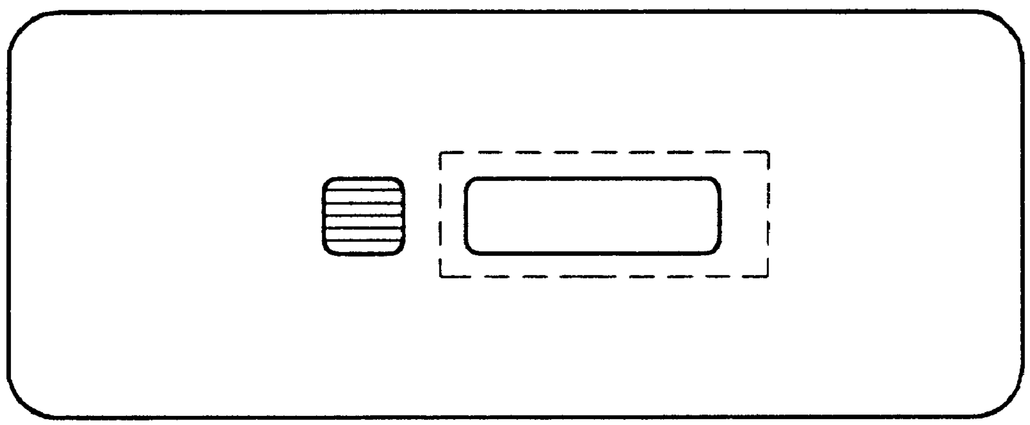
FIG. 10 is an enlarged top view of a device with a porous member between a textured surface nonabsorbent member and an optional member in which the sample is added via a first fluid opening such that the textured surface exposed by the first fluid opening cannot form a capillary network with the porous first member and an additional fluid opening in which the porous member exposed by the additional fluid opening forms a network of capillary channels with the textured surface of the nonabsorbent member.
Figure 11:
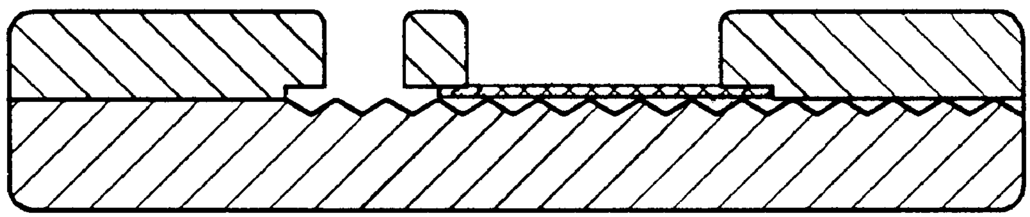
FIG. 11 is a section view, on an enlarged scale, of the device represented in FIG. 10.

In a further preferred embodiment the device comprises in part a porous member, a textured surface nonabsorbent member with an extremity of the textured surface which extends beyond the perimeter of the porous member and an optional member with a first fluid introduction opening located over the portion of the textured surface of the nonabsorbent member which extends beyond the perimeter of the porous member, and an additional fluid opening located over the medial portion of the porous member (FIG. 10 and 11). Sample is introduced to the device through the first fluid opening onto the portion of the textured surface which extends beyond the limits of the porous member. Sample then travels along the channels of the textured surface until reaching the portion of the textured surface which due to contact between the textured surface and the porous member forms the network of capillary channels. Sample then flows within the network of capillary channels or within the porous member according to the relative strengths of the fluid retentive forces of the respective device components and given that the fluid retentive forces favor transfer of sample to the porous member, sample initially contained within the network of capillary channels is spontaneously transferred from the network of capillary channels to the porous member. Additional fluid, if required by the assay protocol, is introduced to the device through the additional fluid opening and when the total volume of fluid added to the device substantially exceeds the void volume of the porous member, fluid transfer is spontaneously initiated such that the fluid in excess of the void volume of the porous member is transferred to the network of capillary channels. In a further particularly preferred embodiment of the device, the total fluid receiving capacity of the device is increased over that of the network of capillary channels by the volume associated with the space enclosed by the nonabsorbent member and the optional member in which the porous member does not intrude.

In the method of the present invention the sample is the first fluid added to the inventive device. Depending on the construction of the assay method, the sample is comprised in part of some or all of the following, ligand receptor, binding agent, specimen-derived target ligand, labeled ligand analogue conjugate, labeled ligand receptor conjugate, free/bound label separation reagents and/or elements of the signal development system. Additional fluids added to the device may contain the remaining reagents necessary to complete the assay procedure. Additional fluid reagents depending on the protocol of the assay method may include but are not limited to ligand receptor, specimen-derived target ligand, labeled ligand analogue conjugate, labeled ligand receptor conjugate, ligand receptor, binding agent, free/bound separation reagents and/or elements of the signal development system. Depending on the structure of the assay protocol several additional fluid reagents may be needed to complete the assay procedure with the composition of successive additional fluid reagents varied as appropriate to the assay protocol. For example in a competitive ligand-receptor assay the sample is comprised in part of specimen-derived target ligand and labeled ligand analogue conjugate. Alternatively, in a displacement competitive ligand receptor assay in which the porous member contains immobilized ligand receptor already complexed with ligand analogue conjugate, the sample is comprised in part of specimen-derived target ligand; whereas in a sequential displacement competitive ligand-receptor assay the sample may be comprised in part of ligand analogue conjugate and specimen-derived target ligand may be added to the device not as sample but as an additional fluid.

In a sequential non-competitive assay method for example, the sample is comprised in part of specimen-derived target ligand. Additional fluid may be comprised in part of labeled ligand receptor conjugate. Further additional fluids may be either separately or in combination comprised in part of free/bound label separation reagents and elements of the signal development system. If the assay is a simultaneous non-competitive method, then the sample may be comprised in part of specimen-derived target ligand and labeled ligand receptor conjugate. Alternatively the sample may be a combination of specimen-derived target ligand, first ligand receptor, and labeled second ligand receptor conjugate. A binding agent may be included to promote immobilization of target ligand or first ligand receptor and their complexes on the porous member. Here too, further additional fluids required by the assay method may be comprised of for example free/bound label separation reagents and/or elements of the signal development system.

In a further preferred embodiment of the inventive device, a competitive ligand-receptor method of the present invention comprises adding sample to the porous member through a first fluid opening located over the medial portion of the porous member. The sample containing specimen-derived target ligand and labeled ligand analogue is allowed to spread over and into the exposed surface of the porous member and is thereby induced to interact with the ligand receptor non-diffusively immobilized upon the porous member. In a preferred embodiment of the inventive device, the ligand receptor is immobilized substantially uniformly in a single zone encompassing the entirety of the porous member. In a particularly preferred embodiment, the ligand receptor is immobilized in at least one discrete zone upon the porous member. In a further particularly preferred embodiment, a multiplicity of ligand receptors are immobilized in a multiplicity of discrete zones each zone containing at least one ligand receptor. In a further particularly preferred embodiment the multiplicity of the discrete zones of ligand receptors is at least as great as the multiplicity of discrete ligands to be determined. A competition is permitted to occur between target ligand and labeled ligand analogue conjugate for the limited binding sites of the immobilized ligand receptor. When the total volume of fluid added to the device is at least sufficient to substantially fill the void volume of the porous member, the fluid in excess of that amount is spontaneously transferred between the porous member and the network of capillary channel created by the contact of the porous member with the textured surface of the nonabsorbent member. The transfer of fluid between the porous and nonabsorbent members facilitates the separation of the labeled ligand analogue conjugate which has complexed with the ligand receptor immobilized on the porous member from the labeled ligand analogue conjugate which did not complex with the ligand receptor immobilized on the porous member. The results of the assay are then judged by the determination of the presence or absence of labeled ligand analogue conjugate within an immobilized ligand receptor zone. When a multiplicity of such discrete ligand receptor zones are present, one can use the devices to simultaneously detect or quantify more than one target ligand of interest. In a further preferred embodiment, if required by the assay protocol, additional fluid which may be comprised in part of either or both of free/bound separation solution or elements of the signal development system is added to the device through a fluid opening.

In another preferred embodiment of the inventive device, the assay method of the present invention may be accomplished as a sequential displacement competitive ligand-receptor protocol. A sample comprised in part of a labeled ligand analogue conjugate is added through the first fluid opening and allowed to interact with the ligand receptor immobilized upon the porous member. An additional fluid comprised in part of specimen-derived target ligand is added to the device through an additional fluid opening and allowed to displace labeled ligand analogue conjugate which has complexed to the ligand receptor immobilized upon the porous member. When the total volume of fluid added to the device is at least sufficient to substantially fill the void volume of the porous member the fluid in excess of that amount is spontaneously transferred between the porous member and the network of capillary channels created by the contact of the porous member with the textured surface of the nonabsorbent member. The assay results are then determined by judging the amount of labeled ligand analogue conjugate within a ligand receptor zone which has not been displaced by specimen-derived target ligand. When a multiplicity of such discrete ligand receptor zones are present, it is possible to detect or quantify one or more target ligands.

In a further embodiment of the present invention, an immunochromatographic method of the present invention comprises adding a sample to the inventive device via the first fluid opening where such opening is located above an extremity of the porous member. The extremity of the porous member is located such that it extends beyond the perimeter of the textured surface of the nonabsorbent member of the inventive device. The sample is comprised in part of specimen-derived target ligand and labeled ligand analogue conjugate which undergo a competition for the limited number of binding sites associated with ligand receptor immobilized on the porous member. In a particularly preferred embodiment of the method, the lower surface of the porous member which extends beyond the textured surface is sealed so that sample is unable to pass through that surface. The sample traverses the porous member confined substantially within the porous structure, originating at a zone proximal to the point of initial sample introduction and progressing to a region of the porous member distal to the point of sample introduction. Labeled ligand analogue conjugate and specimen derived ligand within the sample compete for ligand receptor non-diffusively immobilized upon the porous member during traversal of the porous member. In a preferred embodiment of the invention, the ligand receptor is immobilized substantially uniformly throughout the entirety of the first member. In a particularly preferred embodiment, the ligand receptor is immobilized uniformly within one or more discrete zones along the path of sample traversal. In a further particularly preferred embodiment a multiplicity of ligand receptors are immobilized in a multiplicity of discrete zones each zone containing at least one ligand receptor. In a further particularly preferred embodiment, the multiplicity of the discrete zones of ligand receptors is at least as great as the multiplicity of discrete ligands to be determined. Consequent to traversal of the porous member by the sample, a volume of free/bound label separation solution is added to the medial portion of the porous member via an additional fluid opening to effect the separation of unbound labeled ligand analogue conjugate from labeled ligand analogue conjugate bound to the ligand receptor immobilized on the porous member. The portion of the porous member beneath the additional fluid opening is also in contact with the textured surface of the nonabsorbent member and thereby forms a network of capillary channels. When a sufficient volume of fluid has been introduced into the device, transfer of fluid is spontaneously initiated between the porous member and the network of capillary channels. In a preferred embodiment of the inventive device in which the ligand receptor is uniformly immobilized throughout the entirety of the porous member the results of the assay are judged by a determination of the presence or absence of labeled ligand analogue conjugate which has become immobilized by binding to ligand receptor immobilized on the porous member. In a further preferred embodiment in which the ligand receptor is bound uniformly throughout the entirety of the porous member, the amount of ligand present in the specimen is related to the length of the porous membrane complexed with labeled ligand analogue conjugate. In a particularly preferred embodiment of the inventive device in which the ligand receptor is immobilized within a multiplicity of discrete zones, the amount of ligand within the specimen is related to the number of discrete zones within which labeled ligand analogue conjugate is detected, such zones lying along the path traversed by the fluid sample. The amount of ligand contained within the sample can therefore be related either to the total linear distance complexed with labeled ligand analogue conjugate along a chord connecting the regions proximal to the sample introduction with the region distal to this position when ligand receptor is immobilized substantially uniformly throughout the porous member or may be related to the number of discrete zones within which labeled ligand analogue complexed with ligand receptor is detected, when ligand receptor is immobilized in a number of such discrete ligand receptor zones. In an embodiment in which a multiplicity of ligand receptors are immobilized within a multiplicity of discrete receptor zones, a multiplicity of target ligands may be detected by determination of the presence or absence of signal within particular ligand specific receptor zones.

In a further embodiment of the present invention, a competitive ligand-receptor method of the present invention comprises adding a sample to the porous member of the device through the first fluid opening, where such a sample is comprised in part of ligand receptor, specimen-derived target ligand and labeled ligand analogue conjugate. Prior to addition of the sample to the device the specimen-derived target ligand and labeled ligand analogue conjugate have competed for a limited number of binding sites on the ligand receptor contained within the sample. The sample which is added to the device spreads or wicks over and through the porous member. Target ligand and labeled ligand analogue conjugate which have not bound to the ligand receptor within the sample are able to bind with ligand receptor immobilized upon the porous member. In a preferred embodiment of the invention the ligand receptor is immobilized substantially uniformly throughout the entirety of the porous member. In a particularly preferred embodiment, the ligand receptor is immobilized uniformly within one or more discrete zones upon the porous member. In a further particularly preferred embodiment, a multiplicity of ligand receptors are immobilized in a multiplicity of discrete zones each zone containing at least one ligand receptor. In a further particularly preferred embodiment, the multiplicity of the discrete zones of ligand receptors is at least as great as the multiplicity of discrete zones to be determined. Consequent to incubation of the porous member with the sample, a volume of free/bound label separation solution is added to the porous member via a fluid opening to effect the separation of labeled ligand analogue conjugate which has bound to ligand receptor immobilized upon the porous member from labeled ligand analogue conjugate which has not bound to ligand receptor immobilized on the porous member. Transfer of fluid from the porous member to the network of capillary channels is initiated when the total volume of fluid added to the porous member substantially fills the void volume of the porous member. In a preferred embodiment of the inventive device in which the ligand receptor is uniformly immobilized throughout the entirety of the porous member, the assay results are then determined by inspection of the porous member for the presence or absence of labeled ligand analogue conjugate which has become complexed with immobilized ligand receptor upon the porous member. In a particularly preferred embodiment of the inventive device in which a multiplicity of ligand receptors are immobilized within a multiplicity of discrete zones, a determination is made of which discrete zones have immobilized labeled ligand analogue conjugate.

In a further preferred embodiment, a non-competitive method of the present invention comprises adding a sample to the porous member of the device through the first fluid opening where such a sample is comprised in part of specimen-derived target ligand. The sample is allowed to spread or wick over and into the porous member exposed by the first fluid opening and then into the porous member. Target ligand contained in the sample binds to first ligand receptor immobilized upon the porous member. In a preferred embodiment the first ligand receptor is immobilized substantially uniformly throughout the entirety of the porous member. In a particularly preferred embodiment, the first ligand receptor is immobilized in at least one discrete zone upon the first member. In a further particularly preferred embodiment a multiplicity of first ligand receptors are immobilized in a multiplicity of discrete zones each zone containing at least one ligand receptor. In a further particularly preferred embodiment, the multiplicity of the discrete zones is at least as great as the multiplicity of target ligands to be determined. After allowing the target ligand to bind to the immobilized first ligand receptor, additional fluid containing labeled second receptor conjugate is added to the device through the additional fluid opening. The labeled second receptor conjugate binds to target ligand which has become immobilized upon the porous member by complexation with immobilized first ligand receptor. Labeled second receptor conjugate which has not bound to target ligand immobilized on the porous member is removed by adding free/bound label separation solution to the device through the additional fluid opening. Fluid transfer occurs between the porous member and the network of capillary channels formed by the contact of the porous member with the textured surface of the nonabsorbent member and serves to separate porous member bound second receptor conjugate from unbound second receptor conjugate. If necessary, additional fluid containing elements of the signal development system is added to the device to enable the detection of signal from the label of the bound labeled second receptor conjugate.

In a further preferred embodiment a non-competitive method of the inventive device in which sample comprises in part target ligand that may be derived from cellular material or may be absorbed to particulate binding agents, ligand detection is accomplished by physical entrapment of particulates (e.g. latex particles), by the porous member. The method comprises adding a sample to the porous member of the device through a first fluid opening. The sample is allowed to spread over the surface of the porous member exposed by the first fluid opening and then into the porous member. Target analyte contained within the sample is physically retained by entrapment upon the surface and within the pores of the porous member. Following the physical immobilization of target ligand upon the porous member, additional fluid containing labeled receptor conjugate is added to the device through the additional fluid opening. The labeled receptor conjugate binds to target ligands captured by the porous member. Labeled receptor conjugate which has not bound to target ligand immobilized on the porous member is removed by adding free/bound label separation solution to the device through the additional fluid opening. Fluid transfer between the porous member and the network of capillary channels formed by the contact of the porous member and the textured surface of the nonabsorbent member serves to separate bound labeled receptor conjugate from unbound receptor conjugate. If necessary, an additional fluid containing elements of the signal development system is added to the device to enable detection of the signal from the label of the porous member immobilized labeled receptor conjugate.

The invention has been described in detail with particular reference to the above embodiments. It will be understood, however, that variations and modifications can be effected within the spirit and scope of the invention.

EXAMPLE 1

Preparation of Estrone-3-Glucuron-(2-Amino-A-Thiolbutanoic Acid Thiolacton]-Amide [E3G-HCTL]

77 mg ($1.7\times10^{-4}$ mol) of estrone-3-glucuronide (E3G), 29 mg ($1.9\times10^{-4}$ mol) of homocysteine thiolactone hydrochloride, and 0.015 ml ($1.9\times10^{-4}$ mol) of pyridine were dissolved in 0.47 mL of dimethylformamide. This mixture was added to a solution containing 30 mg ($1.9\times10^{-4}$ mol) dicyclohexylcarbodiimide in 0.23 ml of dimethylformamide. The flask was purged with argon, sealed and stirred at 25° C. for three hours. The insoluble precipitate was filtered and the solvent removed in vacuo. The residue was resuspended in 0.4 mL of an ethanol/water (15:12 v/v) solution and the insoluble precipitates removed by filtration.

The crude reaction mixture was then dissolved in 0.5 mL of an ethanol/water (15:12 v/v) solution and applied to a C18 HPLC column (1 cm×25 cm) equilibrated with a 1:9 mixture of methanol/water using a flow rate of 2.0 mL/min. The compound was eluted with a gradient ramping from a 1:9 mixture of methanol/water to a 1:1 mixture of methanol/water in eight minutes, and was then ramped to a solution of 100% methanol in an additional 20 minutes. E3G-HCTL eluted between 25 and 27 minutes. The fractions containing product were combined and the solvents were removed in vacuo. 63 mg of E3G-HCTL were recovered.

Preparation Of Morphine-Bovine Serum Albumin Conjugate

Seventy-five μL of a solution containing 20 mg of succinimidyl 4-(N-maleimidomethyl)-cyclohexane-1-carboxylate (SMCC) (Pierce) in 1 mL of acetonitrile was added to 1.9 mL of 20 mg/mL bovine serum albumin (BSA) in 0.1M potassium borate, 0.1M potassium phosphate, 0.15M sodium chloride, pH 7.5. The solution was stirred for one hour at 25° C., then the protein was separated from the unreacted reagent by gel filtration chromatography on a column containing GH 25 (Amicon Corporation) equilibrated in 0.1 M potassium phosphate, 0.02M potassium borate, 0.15M sodium chloride, pH 7.0. The protein fraction was collected. A volume of 1.05 mL of 0.12M potassium hydroxide, 0.6 mM ethylenediaminetetraacetic acid (EDTA) in 30% ethanol was added to 100 μL of 210 mN E3G-HCTL in methanol. After five minutes, 1.1 mL of the solution was added to 9.2 mL of the bovine serum albumin derivatized with SMCC (6.5 mg/mL). The solution was stirred for two hours at 25° C., then dialyzed against two changes of one liter of 10 mM (2-(N-morpholino)) ethane sulfonic acid, pH 5.0.

Preparation Of E3G-Colloidal Gold Conjugate

Colloidal gold with an average diameter of 45 nm was prepared according to the method of Frens, *Nature, Physical Sciences,* 241, 20 (1973). E3G-colloidal gold conjugate was prepared by adding 5.6 mL of 0.1M (2-(N-morpholino) ethane sulfonic acid (MES), pH 5.8, dropwise to 50 mL of colloidal gold with rapid stirring. E3G-BSA conjugate (3 mg/mL in 10 mM MES, 0.02% sodium azide, pH 5.8) was added in a bolus to the colloidal gold while stirring rapidly. After complete mixing the stirring was stopped and the solution incubated for 30 minutes at room temperature. The addition of 1 mL of BSA (3 mg/mL in 10 mM MES, 0.02% sodium azide, pH 5.8) with mixing and a five-minute incubation followed. Polyethylene glycol (average molecular weight 20,000 daltons) was added in a 1% solution (0.59 mL) and mixed. The colloidal gold was subjected to centrifugation at 27,000×g for 12 minutes at 4° C. to pellet it. The supernatant was removed and the pellet was washed twice with 35 mL of 10 mM potassium phosphate, 0.01% polyethylene glycol, 0.02% sodium azide, pH 7.0, by resuspending it and subjecting it to centrifugation as described. After the final centrifugation, the pellet was resuspended in 0.5 mL of the buffer and stored at 4° C.

Construction of Device and Demonstration of Free/Bound Conjuate Separation

A nylon membrane (Pall Immunodyne 0.65 μm) was laminated to the underside of an 0.020 inch styrene sheet with a small 0.10"×1.1" rectangular first fluid opening die-cut into the center. A monoclonal antibody against E3G was covalently bound to the activated nylon membrane as a series of three 0.6 μL spots equally spaced within the first fluid opening using the following protein coupling procedure; 1M $PO_4$, 100 mg/mL tetrazole, 50 mM borate, 150 mM NaCl, 1.5 mg/mL antibody, pH 7.4. The membrane was blocked with a solution of 1% w/v casein, and dried overnight in a desiccator. After drying, the laminate assembly was placed on an injection molded part of a styrene copolymer, which included a series of longitudinal 90 degree V-shaped channels that were 0.014 inches wide and 0.007 inches deep. The laminate was then ultrasonically spot welded to the injection molded part.

A 60 $\mu$L sample of E3G colloidal gold conjugate which was not bound to anti-E3G antibody was added to the membrane exposed in the center of the first fluid opening and allowed to absorb into the membrane. A 60 $\mu$L aliquot of E3G colloidal gold conjugate which had been 100% bound with anti-E3G antibody was added to the center of the first fluid opening in another device. In both devices, after the conjugate has been absorbed, 100 $\mu$L of an aqueous wash solution containing 0.05% Lubrol as a surfactant was added to the membrane exposed in the center of the first fluid opening and allowed to flow through the membrane. Immediately after the washing step, the membrane of the first device, to which had been applied E3G-colloidal gold conjugate unbound by anti-E3G antibody, formed a series of three distinct red spots with remainder of the membrane returning to white. In the case of the membrane of the second device, which had utilized 100% bound E3G colloidal gold conjugate, the entire membrane returned to white. This demonstrated that a ligand analogue conjugate was bound specifically by immobilized ligand receptor in a porous member and that the network of capillary channels formed between the porous member and the textured surface non-absorbent member functioned to efficiently wash away any unbound reagents from the porous member.

EXAMPLE 2

Preparation Of Morphine-Alkaline Phosphatase Conjugate

Three mg ($6.9\times10^{-6}$ mol) of sulfo-SMCC (Pierce) was added to 2.2 mL of 4.9 mg/mL alkaline phosphatase in 0.1M potassium phosphate, 0.02M potassium borate, 0.15M sodium chloride, pH 7.5. The protein solution was stirred for one hour at 25° C., then protein was separated from unreacted sulfo-SMCC by gel filtration chromatography on a column containing 40 mL of GH 25 (Amicon Corporation) equilibrated in 0.1M potassium phosphate, 0.02M potassium borate, 0.15M sodium chloride, pH 7.0. The protein fraction eluting from the column was collected. E3G-HCTL was hydrolyzed by adding 20 $\mu$L of 0.12M potassium carbonate, 0.6 mM EDTA in 40% methanol to 13 $\mu$L of 48.5 mM E3G-HCTL in methanol. The solution stood at 25° C. for ten minutes, then 30 $\mu$L of the solution was added to 250 $\mu$L of the alkaline phosphatase derivatized with sulfo-SMCC (3.6 mg/mL) in 0.1M potassium phosphate, 0.02M potassium borate, 0.15M sodium chloride, 0.4 mM magnesium chloride, pH 7.0. The solution was adjusted to pH 7.0 with 1N HCl and then stirred for 30 minutes at 25° C. The protein was separated from the unreacted reagents by gel filtration chromatography as described above. The protein fraction was collected and the conjugate was diluted for use in assays into a solution containing 1% bovine serum albumin, 1 mM magnesium chloride, 0.1 mM zinc chloride, 0.1% sodium azide, and 10 mM 3-(4-morpholino) propane sulfonic acid, pH 7.0.

Construction of Device and Creation of Network of Capillary Channels Subsequent to Addition of Sample A nylon membrane (Pall Immunodyne 0.65 $\mu$m) was laminated to the underside of a 0.020 inch styrene sheet with a small 0.10"×1.1" rectangular first fluid opening die-cut in the center. A monoclonal antibody against E3G was covalently bound to the activated nylon membrane as a series of three 0.6 $\mu$L spots equally spaced in the first fluid opening following the protein coupling procedure; 1M $PO_4$, 100 mg/mL tetrazole, 50 mM borate, 150 mM NaCl, 1.5 mg/mL antibody, pH 7.4; and then blocked with a solution of 1% w/v casein, and dried overnight in a desiccator. After drying, the laminate assembly was positioned such that the underside of the membrane was suspended in air. A 60 $\mu$L aliquot of a conjugate of E3G and alkaline phosphatase which was unbound by anti-E3G antibody was added to the membrane exposed in the center of the first fluid opening and allowed to be absorbed into the membrane. In another membrane laminate, 60 $\mu$L of an E3G-alkaline phosphatase conjugate which had been 100% bound with anti-E3G antibody was added to the center of the first fluid opening.

The laminates were then individually mounted on a photo-etched magneof m alloy plate. The plate contained a series of longitudinal 90° U-shaped channels that were 0.014 inches wide and 0.007 inches deep. Perpendicular-to the longitudinal channels were a series of 127° U-shaped channels that were 0.028 inches wide and 0.007 inches deep. A 100 $\mu$L aliquot of an aqueous wash solution containing 0.05% lubrol as a surfactant was then added to the membrane exposed in the center of the first fluid opening and allowed to flow through the membrane. This was then followed by an addition of 60 $\mu$L of solution containing 10 mM indoxyl phosphate, a substrate for alkaline phosphatase capable of producing a visible color. After two minutes, the membrane of the first device, which had utilized an E3G-alkaline phosphatase conjugate which had been unbound by anti-E3G antibody, formed a pattern of three distinct blue spots; whereas the exposed membrane of the second membrane, which had utilized an E3G-alkaline phosphatase conjugate completely prebound to anti-E3G antibody, remained white. This demonstrated that the network of capillary channels resulting from the contact of the porous and textured surface nonabsorbent members can be formed following the initial addition of the sample to the porous member.

EXAMPLE 3

Preparation of 3-0-[2-Amino-4-Thiolbutanoic Acid Thiolactone)-Acetamide] Morphine Hydrochloride (Morphine-HCTL)

Homocysteine thiolactone hydrochloride 120 mg, ($7.8\times10^{-4}$ mol), 62 mg ($7.8\times10^{-4}$ mol) pyridine, and 296 mg ($7.8\times10^{-4}$ mol) 3-O-carboxymethylmorphine hydrochloride were dissolved in 5 mL dimethylformamide. Addition of 1 mL of a dimethylformamide solution containing 177 mg ($8.6\times10^{-4}$ mol) dicyclohexylcarbodiiside followed. The flask was purged with argon and the solution stirred at 25° C. for three hours. The solvent was evaporated under vacuum and 20 mL water was added to the residue. The solution was stirred for five minutes then the insoluble dicyclohexyl urea was filtered. The filtrate was washed with 10 mL methylene chloride. The pH of the aqueous layer was adjusted to 7 with an aqueous solution of saturated potassium carbonate. The aqueous solution was extracted six times with 10 mL methylene chloride. The combined organic extracts were dried with 2 g magnesium sulfate, filtered, and the solvent removed under vacuum. Ethanol (20 mL) was added to the residue and evaporated under vacuum to remove the pyridine. Ethyl acetate (10 mL) was added and insoluble precipitates were filtered. Ethereal hydrochloric acid (1M) was added to the solution while stirring until the pH was red to litmus. The white solid was filtered and washed with ethyl acetate. The product was dried under vacuum and the yield was 316 mg.

Preparation Of Morphine-Bovine Serum Albumin Conjugate

Seventy-five μL of a solution containing 20 mg of SMCC (Pierce) in 1 mL of acetonitrile was added to 1.9 mL of 20 mg/mL bovine serum albumin in 0.1M potassium borate, 0.1M potassium phosphate, 0.15M sodium chloride, pH 7.5. The solution was stirred for one hour at 25° C., then the protein was separated from the unreacted reagent by gel filtration chromatography on a column containing GH 25 (Amicon Corporation) equilibrated in 0.1M potassium phosphate, 0.02M potassium borate, 0.15M sodium chloride, pH 7.0. The protein fraction was collected. A volume of 0.42 mL of 0.12M potassium carbonate, 0.6 mM EDTA in 40% methanol was added to 4 mg morphine-HCTL. After ten minutes, 140 μL of the solution was added to 8.2 mL of the bovine serum albumin derivatized with SMCC (4.6 mg/mL). The solution was stirred for two hours at 25° C., then dialyzed in two liters of 10 mM (2-(N-morpholino)) ethane sulfonic acid, pH 5.0. The dialysis buffer was changed twice before collecting the morphine-BSA conjugate.

Preparation Of Morphine-Colloidal Gold Conjugate

Colloidal gold with an average diameter of 45 nm was prepared according to the method of Frens, *Nature, Physical Sciences,* 241, 20 (1973). Morphine-colloidal gold conjugate was prepared by adding 5.6 mL of 0.1M (2-(N-morpholino) ethane sulfonic acid (MES), pH 5.8, dropwise to 50 mL of colloidal gold with rapid stirring. Morphine-BSA conjugate (3 mg/mL in 10 mM MES, 0.02% sodium azide, pH 5.8) was added in a bolus to the colloidal gold while stirring rapidly. After complete mixing the stirring was stopped and the solution incubated for 30 minutes at room temperature. The addition of 1 mL of BSA (3 mg/mL in 10 mM MES, 0.02% sodium azide, pH 5.8) with mixing and a five-minute incubation followed. Polyethylene glycol (average molecular weight=20,000 Daltons) was added in a 1% solution (0.59 mL) and mixed. The colloidal gold was subjected to centrifugation at 27,000 g for 12 minutes at 4° C. to pellet it. The supernatant was removed and the pellet was washed twice with 35 mL of 10 mM potassium phosphate, 0.01% polyethylene glycol, 0.02% sodium azide, pH 7.0, by resuspending it and subjecting it to centrifugation as described. After the final centrifugation, the pellet was resuspended in 0.5 mL of the buffer and stored at 4° C.

Construction of Immunochromatographic Device and Demonstration of Immunochromatographic Effect A nylon membrane (Pall Biodyne C 5.0 μm) was laminated to the underside of a 0.020 inch styrene sheet which was die-cut with a small 0.10 inch×1.10 inch additional fluid opening and a 0.10 inch×0.10 inch first fluid opening. A monoclonal antibody against morphine was immobilized on the membrane by adsorption from a solution containing 1% polyvinyl alcohol (MW=2,000 daltons), 50 mM citrate, 1.17 mg/mL antibody, pH 3.0, and the membrane then blocked with a solution of 0.1% w/v casein and 1% polyvinyl alcohol (MW=2,000 daltons) and then dried overnight in a desiccator. After drying, the laminate assembly was placed on an injection molded part of a styrene copolymer, which contained a series of longitudinal 90° V-shaped channels that were 0.014 inches wide and 0.007 inches deep. The laminate was then ultrasonically spot welded to the injection molded part such that the membrane beneath the first fluid opening was not in contact with the textured surface of the nonabsorbent infection molded part.

60 μL aliquots of a series of Morphine-colloidal gold conjugates (relative concentrations of 2, 1.3 and 1) were then added to the first fluid openings of each of three of the devices described above. After the conjugate had migrated the entire length of the window, 100 μL of an aqueous wash solution containing 0.05% lubrol as a surfactant was added to the center of the additional fluid opening and allowed to flow through the membrane. Immediately after the completion of the washing step, a red region appeared on the membrane within the additional fluid opening. The length of the red region varied in proportion with the concentration of the morphine-colloidal gold conjugate. This demonstrated that the labeled species in the sample can be introduced at one end of the porous member and be forced to react with immobilized ligand receptor along the porous member.

Construction of Dome-Shaped Devices

Figure 12:
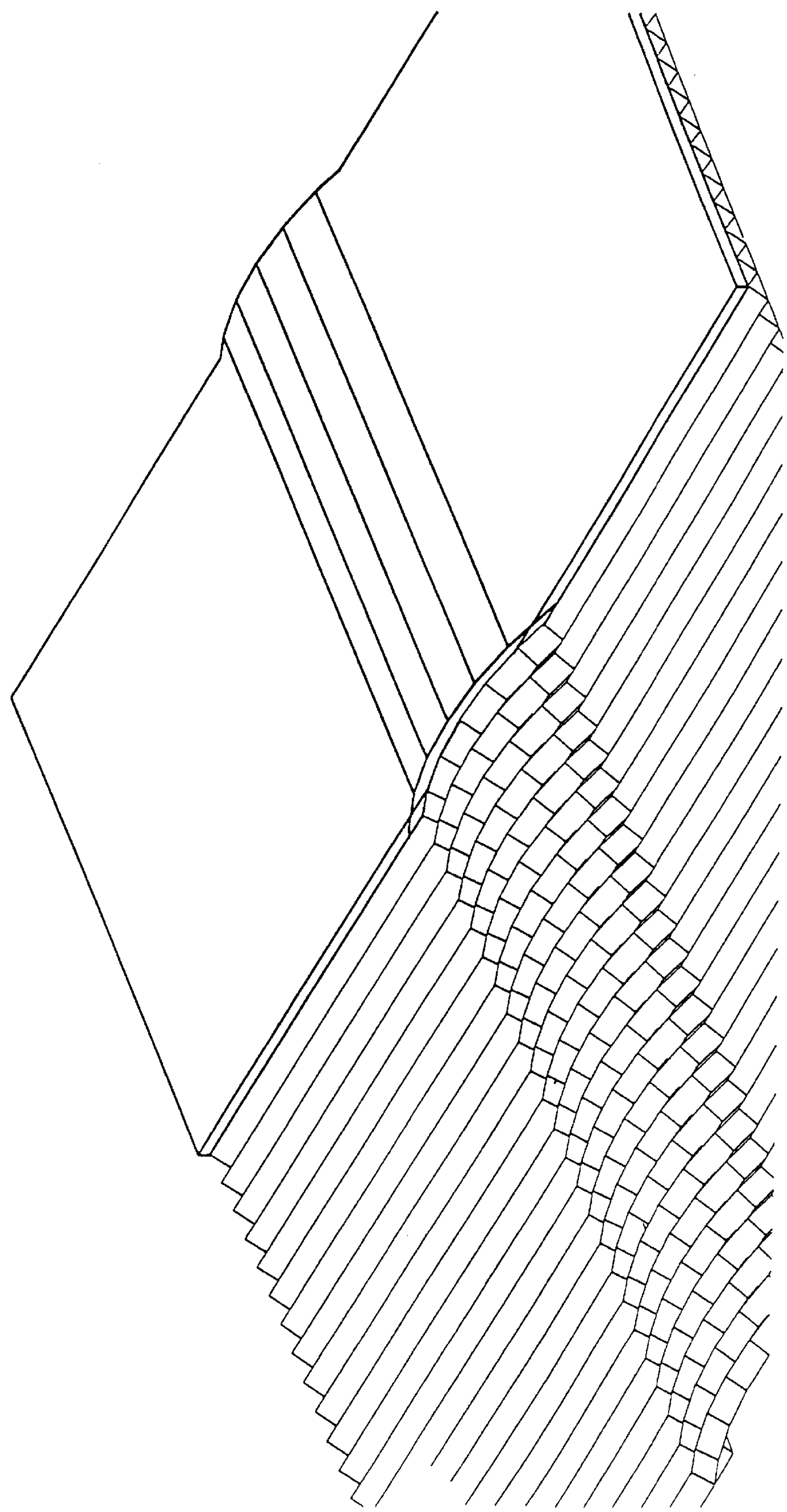
FIG. 12 is an enlarged view from the top of a device with a porous member stretched over a domed nonabsorbent member.
Figure 13:
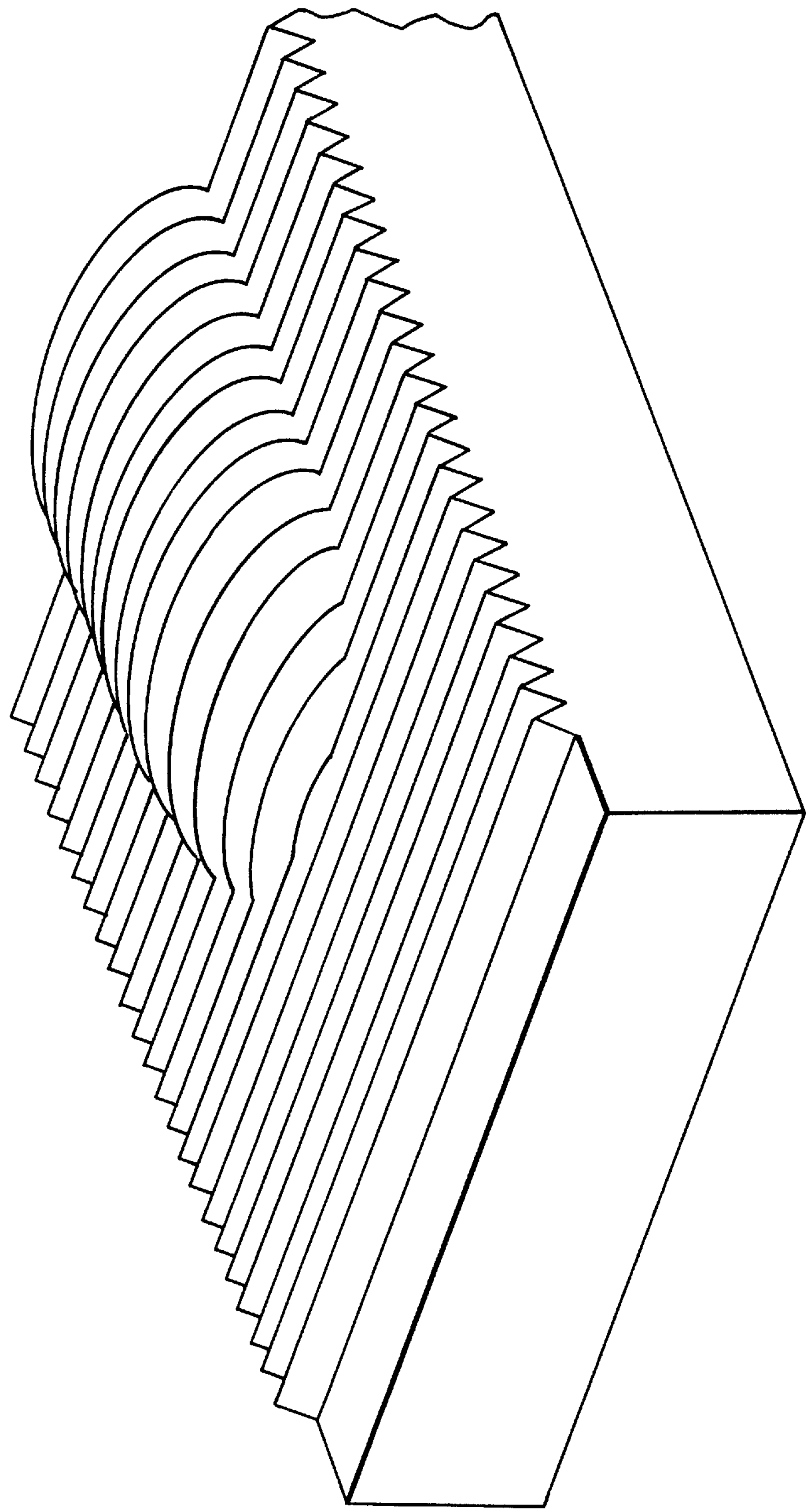
FIG. 13 is an enlarged view of a dome shaped nonabsorbent member.

A particularly preferred embodiment of this invention is a device in which the porous member is stretched over a dome shaped nonabsorbent member. Such devices are illustrated in FIGS. 12 and 13. In such devices, an optional member may be positioned to stretch and hold the porous member over the domed position. This is depicted in FIG. 12. The dome shapes of the nonabsorbent member were of the following varying heights and radii:

| Height | R |
|---|---|
| .005" | 0.305" |
| .010" | 0.155" |
| .019" | 0.090" |

The cord of each of the dome arcs was 0.110". Based on high temperature stress test results, the 0.010" and 0.019" dome heights were preferred to ensure fluid communication between the porous and nonabsorbent members. The surfaces of the domed nonabsorbent members were constructed to have grooves throughout, as depicted in FIG. 12, the grooves being 0.014" wide and 0.007" deep, as depicted in FIG. 12. Optional members with 1.300"× 0.110" openings supported the porous members and exposed the upper surfaces of the porous members of these devices to sample and other fluids.

The domed devices were tested and demonstrated effective in assays.

What is claimed is:

1. A device for performing a heterogeneous assay, comprising, (a) a porous member comprising (i) at least one pore for physically entrapping at least one target ligand in said porous member from a fluid sample in at least one zone and (ii) a diffusively bound labeled reagent for detecting the presence or amount of said at least one target ligand; and (b) a nonabsorbent member in unidirectional fluid communication with said porous member, said nonabsorbent member directly forming at least one capillary channel with said porous member, wherein said fluid communication in said capillary channel is from said porous member to said nonabsorbent member.

2. A device for performing a heterogeneous assay, comprising:

(a) a porous member comprising (i) at least one binding agent immobilized in at least one zone said at least one binding agent capable of immobilizing by specific binding at least one target ligand in said porous member from a fluid sample in said at least one zone and (ii) a diffusively bound labeled reagent for detecting the presence or amount of said at least one target ligand; and (b) a nonabuorbent member in unidirectional fluid communication with said porous member, said nonabsorbent member directly forming at least one capillary channel with said porous members, wherein said fluid communication in said capillary channel is from said porous member to said nonabsorbent member.

3. A device for performing a heterogeneous assay, comprising:

(a) a porous member comprising (i) at least one ligand receptor immobilized in at least one zone said at least one ligand receptor capable of immobilizing by specific binding at least one target ligand in said porous member from a fluid sample in said at least one zone and (ii) a diffusively bound labeled reagent for detecting the presence or amount of said at least one target ligand; and (b) a nonabsorbent member in unidirectional fluid communication with said porous member, said nonabsorbent member directly forming at least one capillary channel with said porous member, wherein said fluid communication in said capillary channel is from said porous member to said nonabsorbent member.

4. A device for performing a heterogeneous assay, comprising:

(a) a porous member comprising (i) at least one ligand receptor immobilized in at least one zone said at least one ligand receptor capable of immobilizing by specific binding at least one ligand analogue conjugate or at least one target ligand in said porous member such that said at least one ligand analogue conjugate is immobilized in an amount related to the amount of said at least one target ligand in a fluid sample in said at least one zone and (ii) said at least one ligand analogue conjugate, diffusively bound in said porous member, for detecting the presence or amount of said at least one target ligand; and (b) a nonabsorbent member in undirectional fluid communication with said porous member, said nonabsorbent member directly forming at least one capillary channel with said porous member, wherein said fluid communication in said capillary channel is from said porous member to said nonabsorbent member.

5. A device for performing a heterogeneous assay, comprising:

(a) a porous member comprising (i) at least one pore for physically entrapping at least one target ligand in said porous member from a fluid sample in at least one zone and (ii) a diffusively bound labeled reagent for detecting the presence or amount of said at least one target ligand; and (b) a nonabsorbent member in unidirectional fluid communication with said porous member, said nonabsorbent member directly forming a network of capillary channels with said porous member, wherein said fluid communication in said capillary channel is from said porous member to said nonabsorbent member.

6. A device for performing a heterogeneous assay, comprising:

(a) a porous member comprising (i) at least one binding agent immobilized in at least one zone said at least one binding agent capable of immobilizing by specific binding at least one target ligand in said porous member from a fluid sample in said at least one zone and (ii) a diffusively bound labeled reagent for detecting the presence or amount of said at least one target ligand; and (b) a nonabsorbent member in unidirectional fluid communication with said porous member, said nonabsorbent member directly forming a network of capillary channels with said porous member, wherein said fluid communicaion in said capillary channel is from said porous member to said nonabsorbent member.

7. A device for performing a heterogeneous assay, comprising:

(a) a porous member comprising (i) at least one ligand receptor immobilized in at least one zone said at least one ligand receptor capable of immobilizing by specific binding at least one target ligand in said porous member from a fluid sample in said at least one zone and (ii) a diffusively bound labeled reagent for detecting the presence or amount of said at least one target ligand; and (b) a nonabsorbent member in unidirectional fluid communication with said porous member, said nonabsorbent member directly forming a network of capillary channels, with said porous member, wherein said fluid communication in said capillary channel is from said porous member to said nonabsorbent member.

8. A device for performing a heterogeneous assay, comprising:

(a) a porous member comprising (i) at least one ligand receptor immobilized in at least one zone said at least one ligand receptor capable of immobilizing by specific binding at least one ligand analogue conjugate or at least one target ligand in said porous member such that said at least one ligand analogue conjugate is immobilized in an amount related to the amount of said at least one target ligand in a fluid sample in said at least one zone and (ii) said ligand analogue conjugate, deffusively bound in said porous member, for detecting the presence or amount of said at least one target ligand; and (b) a nonabsorbent member in unidirectional fluid communication with said porous member, said nonabsorbent member directly forming a network of capillary channels with said porous member, wherein said fluid communiation in said capillary channel is from said porous member to said nonabsorbent member.

9. A device for performing a heterogeneous assay, comprising:

(a) a porous member comprising (i) at least one pore for physically entrapping at least one target ligand in said porous member from a fluid sample in at least one zone and (ii) a diffusively bound labeled reagent for detecting the presence or amount of said at least one target ligand;

(b) a nonabsorbent member in unidirectional fluid communication with said porous member, said nonabsorbent member directly forming at least one capillary channel with said porous member, wherein said fluid communication in said capillary channel is from said porous member to said nonabsorbent member; and (c) a nonabsorbent third member disposed substantially above or around said porous member (a), with at least one opening to access said porous member, such that fluids applied to said opening wick over or into said porous member.

10. A device for performing a heterogeneous assay, comprising:

(a) a porous member comprising (i) at least one binding agent immobilized in at least one zone said at least one binding agent capable of immobilizing by specific binding at least one target ligand in said porous member from a fluid sample in said at least one zone and (ii) a diffusively bound labeled reagent for detecting the presence or amount of said at least one target ligand;

(b) a nonabsorbent member in unidirectional fluid communication with said porous member, said nonabsorbent member directly forming at least one capillary channel with said porous member, wherein said fluid communication in said capillary channel is from said porous member to said nonabsorbent member; and (c) a nonabsorbent third member disposed substantially above or around said porous member (a), with at least one opening to access said porous member, such that fluids applied to said opening wick over or into said porous member.

11. A device for performing a heterogeneous assay, comprising:

(a) a porous member comprising (i) at least one ligand receptor immobilized in at least one zone said at least one ligand receptor capable of immobilizing by specific binding at least one target ligand in said porous member from a fluid sample in said at least one zone and (ii) a diffusively bound labeled reagent for detecting the presence or amount of said at least one target ligand;

(b) a nonabsorbent member in unidirectional fluid communication with said porous member, said nonabsorbent member directly forming at least one capillary channel with said porous member, wherein said fluid communication in said capillary channel is from said porous member to said nonabsorbent member; and (c) a nonabsorbent third member disposed substantially above or around said porous member (a), with at least one opening to access said porous member, such that fluids applied to said opening wick over or into said porous member.

12. A device for performing a heterogeneous assay, comprising:

(a) a porous member comprising (i) at least one ligand receptor immobilized in at least one zone said at least one ligand receptor capable of immobilizing by specific binding at least one ligand analogue conjugate or at least one target ligand in said porous member such that said at least one ligand analogue conjugate is immobilized in an amount related to the amount of said at least one target ligand in a fluid sample in said at least one zone and (ii) said at least one ligand analogue conjugate, deffusinely bound in said porous member, for detecting the presence or amount of said at least one target ligand;

(b) a nonabsorbent member in unidirectional fluid communication with said porous member, said nonabsorbent member directly forming at least one capillary channel with said porous member, wherein said fluid communication in said capillary channel is from said porous member to said nonabsorbent member; and (c) a nonabsorbent third member disposed substantially above or around said porous member (a), with at least one opening to access said porous member, such that fluids applied to said opening wick over or into said porous member.

13. A device for performing a heterogeneous assay, comprising:

(a) a porous member comprising (i) at least one pore for physically entrapping at least one target ligand in said porous member from a fluid sample in at least one zone and (ii) a diffusively bound labeled reagent for detecting the presence or amount of said at least one target ligand;

(b) a nonabsorbent member in unidirectional fluid communication with said porous member, said nonabsorbent member directly forming a network of capillary channels with said porous member, wherein said fluid communication in said capillary channel is from said porous member to said nonabsorbent member; and (c) a nonabsorbent third member disposed substantially above or around said porous member (a), with at least one opening to access said porous member, such that fluids applied to said opening wick over or into said porous member.

14. A device for performing a heterogeneous assay, comprising:

(a) a porous member comprising (i) at least one binding agent immobilized in at least one zone said at least one binding agent capable of immobilizing by specific binding at least one target ligand in said porous member from a fluid sample in said at least one zone and (ii) a diffusively bound labeled reagent for detecting the presence or amount of said at least one target ligand;

(b) a nonabsorbent member in unidirectional fluid communication with said porous member, said nonabsorbent member directly forming a network of capillary channels with said porous member, wherein said fluid communication in said capillary channel is from said porous member to said nonabsorbent member; and (c) a nonabsorbent third member disposed substantially above or around said porous member (a), with at least one opening to access said porous member, such that fluids applied to said opening wick over or into said porous member.

15. A device for performing a heterogeneous assay, comprising:

(a) a porous member comprising (i) at least one ligand receptor immobilized in at least one zone said at least one ligand receptor capable of immobilizing by specific binding at least one target ligand in said porous member from a fluid sample in said at least one zone and (ii) a diffusively bound labeled reagent for detecting the presence or amount of said at least one target ligand;

(b) a nonabsorbent member in unidirectional fluid communication with said porous member, said nonabsorbent member directly forming a network of capillary channels with said porous member, wherein said fluid communication in said capillary channel is from said porous member to said nonabsorbent member; and (c) a nonabsorbent third member disposed substantially above or around said porous member (a), with at least one opening to access said porous member, such that fluids applied to said opening wick over or into said porous member.

16. A device for performing a heterogeneous assay, comprising:

(a) a porous member comprising (i) at least one ligand receptor immobilized in at least one zone said at least one ligand receptor capable of immobilizing by specific binding at least one ligand analogue conjugate or at least one target ligand in said porous member such that said at least one ligand analogue conjugate is immobilized in an amount related to the amount of said at least one target ligand in a fluid sample in said at least one zone and (ii) said at least one ligand analogue conjugate, deffusively bound in said porous member, for detecting the presence or amount of said target ligand;

(b) a nonabsorbent member in unidirectional fluid communication with said porous member, said nonabsorbent member directly forming a network of capillary channels with said porous member, wherein said fluid communication in said capillary channel is from said porous member to said nonabsorbent member; and (c) a nonabsorbent third member disposed substantially above or around said porous member (a), with at least one opening to access said porous member, such that fluids applied to said opening wick over or into said porous member.

17. The device of claims 2, 6, 10, or 14 wherein said at least one binding agent is a monoclonal antibody that specifically binds to said at least one target ligand.

18. The device of claims 3, 4, 7, 8, 11, 12, 15, or 16 wherein said at least one ligand receptor is a monoclonal antibody.

19. The device as in any of claims 1–16 wherein said porous member is a nylon membrane.

20. A method of assaying for a target ligand comprising the steps of:

(a) contacting a volume of a sample with a device, said device comprising (i) a porous member comprising a pore for physically entrapping said target ligand from said sample, and (ii) a nonabsorbent member in unidirectional fluid communication with said porous member, said nonabsorbent member directly forming a capillary channel with said porous member so that when the sample, alone or in combination with other fluids, is contacted with said porous member, fluid is drawn through said porous member to said nonabsorbent member, (b) contacting a volume of a labeled reagent with said device so that said labeled reagent specifically binds to entrapped target ligand; and (c) relating the amount of said labeled reagent specifically bound to said entrapped target ligand to the presence or amount of said target ligand in said sample.

21. A method of assaying for a target ligand comprising the steps of:

(a) contacting a volume of a sample with a device, said device comprising (i) a porous member comprising a pore for physically entrapping said target ligand from said sample, and (ii) a nonabsorbent member in unidirectional fluid communication with said porous member, said nonabsorbent member directly forming a network of capillary channels with said porous member so that when the sample, alone or in combination with other fluids, is added to said porous member, fluid is drawn through said porous member to said nonabsorbent member;

(b) contacting a volume of a labeled reagent with said device so that said labeled reagent specifically binds to entrapped target ligand; and (c) relating the amount of said labeled reagent specifically bound to said entrapped target ligand to the presence or amount of said target ligand in said sample.

22. The method of claim 20, wherein said device further comprises a nonabsorbent third member disposed substantially above or around said porous member, with at least one opening to access said porous member, such that fluids applied to said opening wick over or into said porous member.

23. The method of claim 21, wherein said device further comprises a nonabsorbent third member disposed substantially above or around said porous member, with at least one opening to access said porous member, such that fluids applied to said opening wick over or into said porous member.

24. A method of assaying for a target ligand comprising the steps of:

(a) contacting a volume of a sample with a device, said device comprising (i) a porous member and a binding agent immobilized in said porous member, said binding agent for immobilizing by specific binding said target ligand in said porous member, and (ii) a nonabsorbent member in unidirectional fluid communication with said porous member, said nonabsorbent member directly forming a capillary channel with said porous member so that when the sample, alone or in combination with other fluids, is added to said porous member, fluid is drawn through said porous member to said nonabsorbent member, (b) contacting a volume of a labeled reagent with said device so that said labeled reagent specifically binds to immobilized target ligand; and (c) relating the amount of said labeled reagent specifically bound to said immobilized target ligand to the presence or amount of said target ligand in said sample.

25. A method of assaying for a target ligand comprising the steps of:

(a) contacting a volume of a sample with a device, said device comprising (i) a porous member and a binding agent immobilized in said porous member, said binding agent for immobilizing by specific binding said target ligand in said porous member, and (ii) a nonabsorbent member in unidirectional fluid communication with said porous member, said nonabsorbent member directly forming a network of capillary channels with said porous member so that when the sample, alone or in combination with other fluids, is added to said porous member, fluid is drawn through said porous member to said nonabsorbent member, (b) contacting a volume of a labeled reagent with said device so that said labeled reagent specifically binds to immobilized target ligand; and (c) relating the amount of said labeled reagent specifically bound to said immobilized target ligand to the presence or amount of said target ligand in said sample.

26. The method of claim 24, wherein said device further comprises a nonabsorbent third member disposed substantially above or around said porous member, with at least one opening to access said porous member, such that fluids applied to said opening wick over or into said porous member.

27. The method of claim 25, wherein said device further comprises a nonabsorbent third member disposed substantially above or around said porous member, with at least one opening to access said porous member, such that fluids applied to said opening wick over or into said porous member.

28. A method of assaying for a target ligand comprising the steps of:

(a) contacting a volume of a sample with a device, said device comprising (i) a porous member and a receptor immobilized in said porous member, said receptor for immobilizing by specific binding said target ligand in said porous member, and (ii) a nonabsorbent member in unidirectional fluid communication with said porous member, said nonabsorbent member directly forming a capillary channel with said porous member so that when the sample, alone or in combination with other fluids, is added to said porous member, fluid is drawn through said porous member to said nonabsorbent member, (b) contacting a volume of a labeled reagent with said device so that said labeled reagent specifically binds to immobilized target ligand; and (c) relating the amount of said labeled reagent specifically bound to said immobilized target ligand to the presence or amount of said target ligand in said sample.

29. A method of assaying for a target ligand comprising the steps of:

(a) contacting a volume of a sample with a device, said device comprising (i) a porous member and a receptor immobilized in said porous member, said receptor for immobilizing by specific binding said target ligand in said porous member, and (ii) a nonabsorbent member in unidirectional fluid communication with said porous member, said nonabsorbent member directly forming a network of capillary channels with said porous member so that when the sample, alone or in combination with other fluids, is added to said porous member, fluid is drawn through said porous member to said nonabsorbent member, (b) contacting a volume of a labeled reagent with said device so that said labeled reagent specifically binds to immobilized target ligand; and (c) relating the amount of said labeled reagent specifically bound to said immobilized target ligand to the presence or amount of said target ligand in said sample.

30. The method of claim 28, wherein said device further comprises a nonabsorbent third member disposed substantially above or around said porous member, with at least one opening to access said porous member, such that fluids applied to said opening wick over or into said porous member.

31. The method of claim 29, wherein said device further comprises a nonabsorbent third member disposed substantially above or around said porous member, with at least one opening to access said porous member, such that fluids applied to said opening wick over or into said porous member.

32. A method of assaying for a target ligand in a sample comprising the steps of:

(a) contacting a volume of said sample with a first receptor and a second labeled ligand receptor that both specifically bind said target ligand, to form a reaction mixture;

(b) contacting a volume of said reaction mixture with a device, said device comprising (i) a porous member and a binding agent immobilized in said porous member said binding agent for immobilizing by specific binding said first receptor in said porous member, and (ii) a nonabsorbent member in unidirectional fluid communication with said porous member, said nonabsorbent member directly forming a capillary channel with said porous member so that when said reaction mixture, alone or in combination with other fluids, is added to said porous member, fluid is drawn through said porous member to said nonabsorbent member; and (c) relating the amount of said second labeled ligand receptor specificaly bound to said binding agent to the presence or amount of said target ligand in said sample.

33. A method of assaying for a target ligand in a sample comprising the steps of:

(a) contacting a volume of said sample with a first receptor and a second labeled ligand receptor that both specifically bind said target ligand, to form a reaction mixture;

(b) contacting a volume of said reaction mixture with a device, said device comprising (i) a porous member and a binding agent immobilized in said porous member, said binding agent for immobilizing by specific binding said first receptor in said porous member, and (ii) a nonabsorbent member in unidirectional fluid communication with said porous member, said nonabsorbent member directly forming a network of capillary channels with said porous member so that when said reaction mixture, alone or in combination with other fluids, is added to said porous member, fluid is drawn through said porous member to said nonabsorbent member; and (c) relating the amount of said labeled ligand receptor specifically bound to said binding agent to the presence or amount of said target ligand in said sample.

34. The method of claim 32, wherein said device further comprises a nonabsorbent third member disposed substantially above or around said porous member, with at least one opening to access said porous member, such that fluids applied to said opening wick over or into said porous member.

35. The method of claim 33, wherein said device further comprises a nonabsorbent third member disposed substantially above or around said porous member, with at least one opening to access said porous member, such that fluids applied to said opening wick over or into said porous member.

36. A method of assaying for a target ligand in a sample comprising the steps of:

(a) contacting a volume of the sample with a device, said device comprising (i) a porous member and a receptor immobilized in said porous member said receptor for immobilizing by specific binding said target ligand or a ligand analogue conjugate in said porous member, and (ii) a nonabsorbent member in unidirectional fluid communication with said porous member, said nonabsorbent member directly forming a capillary channel with said porous member so that when the sample, alone or in combination with other fluids, is added to said porous member, fluid is drawn through said porous member to said nonabsorbent member, (b) contacting a volume of said ligand analogue conjugate to said device so that said ligand analogue conjugate specifically binds to said receptor; and (c) relating the amount of said ligand analogue conjugate specifically bound to said receptor to the presence or amount of said target ligand in said sample.

37. A method of assaying for a target ligand in a sample comprising the steps of:

(a) contacting a volume of a sample with a device, said device comprising (i) a porous member and a receptor immobilized in said porous member said receptor for immobilizing by specific binding said target ligand or a ligand analogue conjugate in said porous member, and (ii) a nonabsorbent member in unidirectional fluid communication with said porous member, said nonabsorbent member directly forming a network of capillary channels with said porous member so that when the sample, alone or in combination with other fluids, is added to said porous member, fluid is drawn through said porous member to said nonabsorbent member, (b) contacting a volume of said ligand analogue conjugate with said device so that said ligand analogue conjugate specifically binds to said receptor; and (c) relating the amount of ligand analogue conjugate specifically bound to said receptor to the presence or amount of said target ligand in said sample.

38. The method of claim 36, wherein said device further comprises a nonabsorbent third member disposed substantially above or around said porous member, with at least one opening to access said porous member, such that fluids applied to said opening wick over or into said porous member.

39. The method of claim 37, wherein said device further comprises a nonabsorbent third member disposed substantially above or around said porous member, with at least one opening to access said porous member, such that fluids applied to said opening wick over or into said porous member.

40. A method of assaying for a target ligand in a sample comprising the steps of:

(a) contacting a volume of said sample with a ligand analogue conjugate and a receptor so that said receptor specifically binds said target ligand and said ligand analogue conjugate, to form a reaction mixture;

(b) contacting a volume of said reaction mixture with a device, said device comprising (i) a porous member and a binding agent immobilized in said porous member said binding agent for immobilizing by specific binding said receptor in said porous member, and (ii) a nonabsorbent member in unidirectional fluid communication with said porous member, said nonabsorbent member directly forming a capillary channel with said porous member so that when the reaction mixture, alone or in combination with other fluids, is added to said porous member, fluid is drawn through said porous member to said nonabsorbent member; and (c) relating the amount of said ligand analogue conjugate specifically bound to said binding agent to the presence or amount of said target ligand in said sample.

41. A method of assaying for a target ligand in a sample comprising the steps of:

(a) contacting a volume of said sample with a ligand analogue conjugate and a receptor so that said receptor specifically binds said target ligand and said ligand analogue conjugate to form a reaction mixture;

(b) contacting a volume of said reaction mixture with a device, said device comprising (i) a porous member and a binding agent immobilized in said porous member, said binding agent for immobilizing by specific binding said receptor in said porous member, and (ii) a nonabsorbent member in unidirectional fluid communication with said porous member, said nonabsorbent member directly forming a network of capillary channels with said porous member so that when the reaction mixture, alone or in combination with other fluids, is added to said porous member, fluid is drawn through said porous member to said nonabsorbent member, (c) relating the amount of said ligand analogue conjugate specifically bound to said binding agent to the presence or amount of said target ligand in said sample.

42. The method of claim 40, wherein said device further comprises a nonabsorbent third member disposed substantially above or around said porous member, with at least one opening to access said porous member, such that fluids applied to said opening wick over or into said porous member.

43. The method of claim 41, wherein said device further comprises a nonabsorbent third member disposed substantially above or around said porous member, with at least one opening to access said porous member, such that fluids applied to said opening wick over or into said porous member.

44. A method of assaying for a target ligand in a sample comprising the steps of:

(a) contacting a volume of said sample with a ligand analogue conjugate and a receptor so that said receptor specifically binds said target ligand and said ligand analogue conjugate, to form a reaction mixture;

(b) contacting a volume of said reaction mixture with a device, said device comprising (i) a porous member and a second receptor immobilized in said porous member said second receptor for immobilizing by specific binding said ligand analogue conjugate in said porous member, and (ii) a nonabsorbent member in unidirectional fluid communication with said porous member, said nonabsorbent member directly forming a capillary channel with said porous member so that when the reaction mixture, alone or in combination with other fluids, is added to said porous member, fluid is drawn through said porous member to said nonabsorbent member, and (iii) a nonabsorbent third member disposed substantially above or around said porous member (i), with at least one opening to access said porous member, such that fluids applied to said opening wick over or into said porous member; and (c) relating the amount of said ligand analogue conjugate specifically bound to said second receptor to the presence or amount of said target ligand in said sample.

45. A method of assaying for a target ligand in a sample comprising the steps of:

(a) contacting a volume of said sample with a ligand analogue conjugate and a first receptor so that said receptor specifically binds said target ligand and said ligand analogue conjugate to form a reaction mixture;

(b) contacting a volume of said reaction mixture with a device, said device comprising (i) a porous member and a second receptor immobilized in said porous member, said second receptor for immobilizing by specific binding said ligand analogue conjugate in said porous member, and (ii) a nonabsorbent member in unidirectional fluid communication with said porous member, said nonabsorbent member directly forming a network of capillary channels with said porous member so that when the reaction mixture, alone or in combination with other fluids, is added to said porous member, fluid is drawn through said porous member to said nonabsorbent member, and (iii) a nonabsorbent third member disposed substantially above or around said porous member with at least one opening to access said porous member, such that fluids applied to said opening wick over or into said porous member; and (c) relating the amount of said ligand analogue conjugate specifically bound to said second receptor to the presence or amount of said target ligand in said sample.

* * * * *